(12) United States Patent
Miura

(10) Patent No.: US 7,985,852 B2
(45) Date of Patent: Jul. 26, 2011

(54) HTERT GENE EXPRESSION REGULATORY GENE

(75) Inventor: Norimasa Miura, Tottori (JP)

(73) Assignee: National University Corporation Tottori University, Tottori (JP)

(*) Notice: Subject to any disclaimer, the term of this patent is extended or adjusted under 35 U.S.C. 154(b) by 663 days.

(21) Appl. No.: 11/911,364

(22) PCT Filed: Mar. 28, 2006

(86) PCT No.: PCT/JP2006/306338
§ 371 (c)(1),
(2), (4) Date: Jan. 22, 2008

(87) PCT Pub. No.: WO2006/112239
PCT Pub. Date: Oct. 26, 2006

(65) Prior Publication Data
US 2009/0124794 A1    May 14, 2009

(30) Foreign Application Priority Data
Apr. 15, 2005 (JP) ................... 2005-118364

(51) Int. Cl.
*C07H 21/04* (2006.01)
*C12N 15/00* (2006.01)
(52) U.S. Cl. .................. 536/24.5; 435/320.1
(58) Field of Classification Search .......... None
See application file for complete search history.

(56) References Cited

U.S. PATENT DOCUMENTS

| 2003/0144232 | A1 | 7/2003 | Agami et al. | |
|---|---|---|---|---|
| 2003/0144239 | A1 | 7/2003 | Agami et al. | |
| 2007/0031844 | A1* | 2/2007 | Khvorova et al. | 435/6 |

FOREIGN PATENT DOCUMENTS

| GB | 2 383 330 | 6/2003 |
|---|---|---|
| JP | 2004-350607 | 12/2004 |
| JP | 2005-512596 | 5/2005 |
| JP | 2005-524393 | 8/2005 |
| WO | 03/056012 | 7/2003 |
| WO | 03/070744 | 8/2003 |
| WO | 2004/048566 | 6/2004 |

OTHER PUBLICATIONS

GenBank AL355591, Jun. 20, 2002.*
Peck, A.: Title: Direct Submission, Definition: Human DNA sequence from clone RP110-300b7 on chromosome 10 Contains a CpG island, complete sequence; dated Apr. 30, 2008; Database EMBL Jun. 21, 2002, XP002487838, Database accession No. al355591.
"Supplementary European Search Report" dated Jun. 21, 2002 (EP 06 73 0286).
Arata Nishimoto et al., "Functional evidence for a telomerase repressor gene on human chromosome 10p15.1," Oncogene, 2001, vol. 20, No. 7, pp. 828-835.
Hiromi Tanaka et al., "Evidence for a putative telomerase repressor gene in the 3p142-p21.1 Region," Genes, Chromosomes & Cancer, 1998, vol. 23, No. 2, pp. 123-133.
Joseph C. Poole et al., "Activity, function, and gene regulation of the catalytic subunit of telomerase (hTERT)," Gene, 2001, vol. 269, Nos. 1 and 2, pp. 1-12.
Shuwen Wang et al., "Evidence for a relief of repression mechanism for activation of the human telomerase reverse transcriptase promoter," The Journal of Biological Chemistry, 2003, vol. 278, No. 21, pp. 18842-18850.
Jaejoon Won et al., "Opposing regulatory roles of E2F in human telomerase reverse transcriptase (hTERT) gene expression in human tumor and normal somatic cells," FASEB.J., 2002, vol. 16, No. 14, pp. 1943-1945.
Ahmet M. Denli et al., "Processing of primary microRNAs by the microprocessor complex," Letters to Nature, 2004, vol. 432, No. 7014, pp. 231-235.

* cited by examiner

*Primary Examiner* — Richard Schnizer
(74) *Attorney, Agent, or Firm* — Pearne & Gordon LLP

(57) ABSTRACT

Disclosed is a novel substance capable of regulating the expression of a telomerase reverse transcriptase gene in a cell of a mammal. A gene capable of regulating the expression of hTERT, comprising a nucleotide sequence depicted in SEQ ID No: 1 or 2. The expression of a telomerase reverse transcriptase gene can be inhibited by inhibiting the expression of the gene. By utilizing this mechanism, the expression of a telomerase reverse transcriptase gene can be regulated.

8 Claims, 29 Drawing Sheets

Cloning of RGM376
After micro nuclear fusion method and BAC screening,
Exon trapping was performed 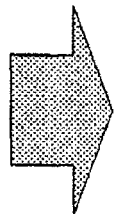 Telomerase was activated by forced expression
Exon suppressing hTERT mRNA expression was identified 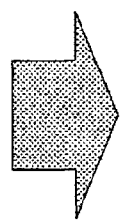 As a result of investigation of base sequence, ORF analysis, and in vitro translation, it was found to be a ncRNA that does not synthesize protein.
fig 2

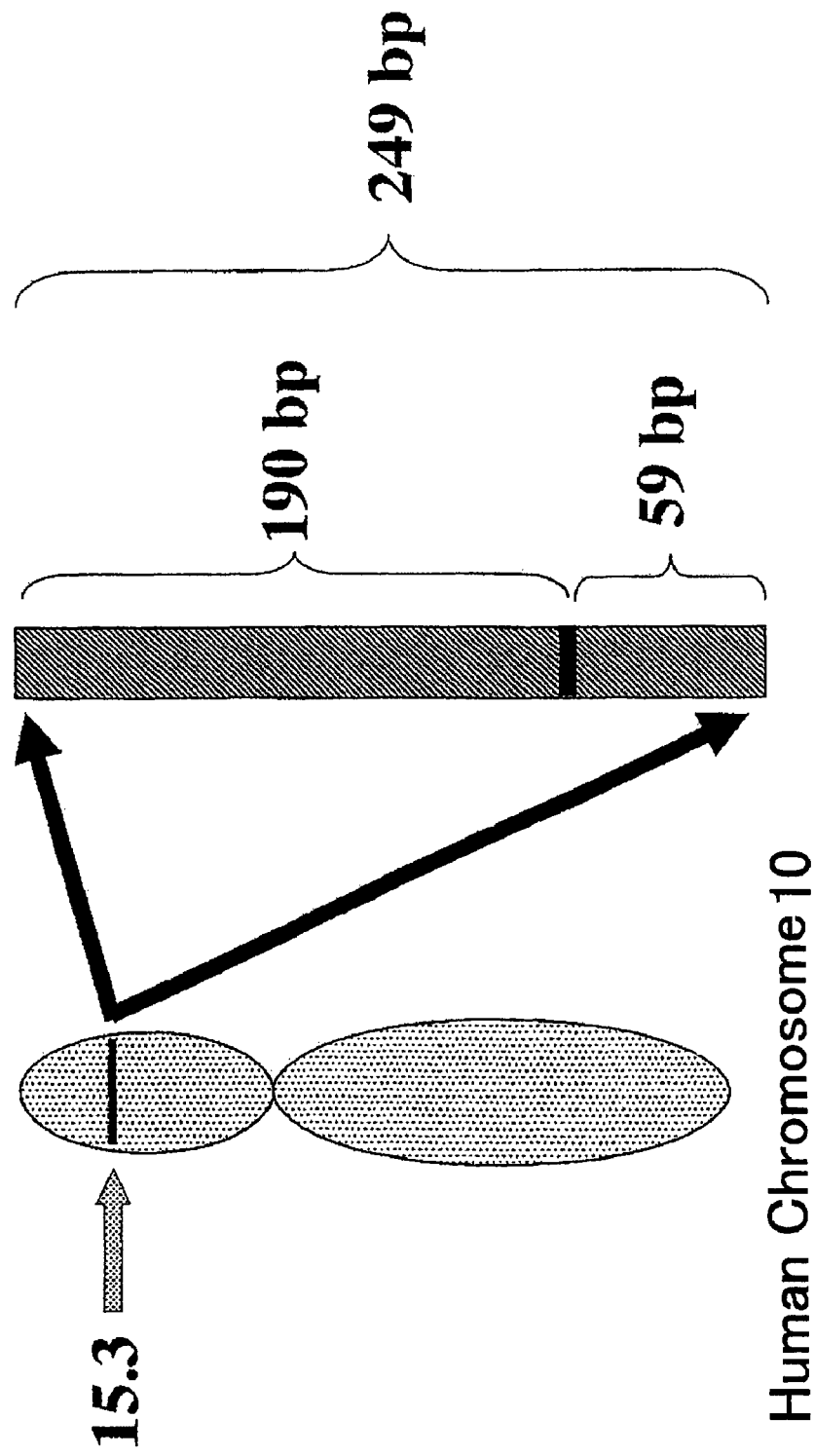

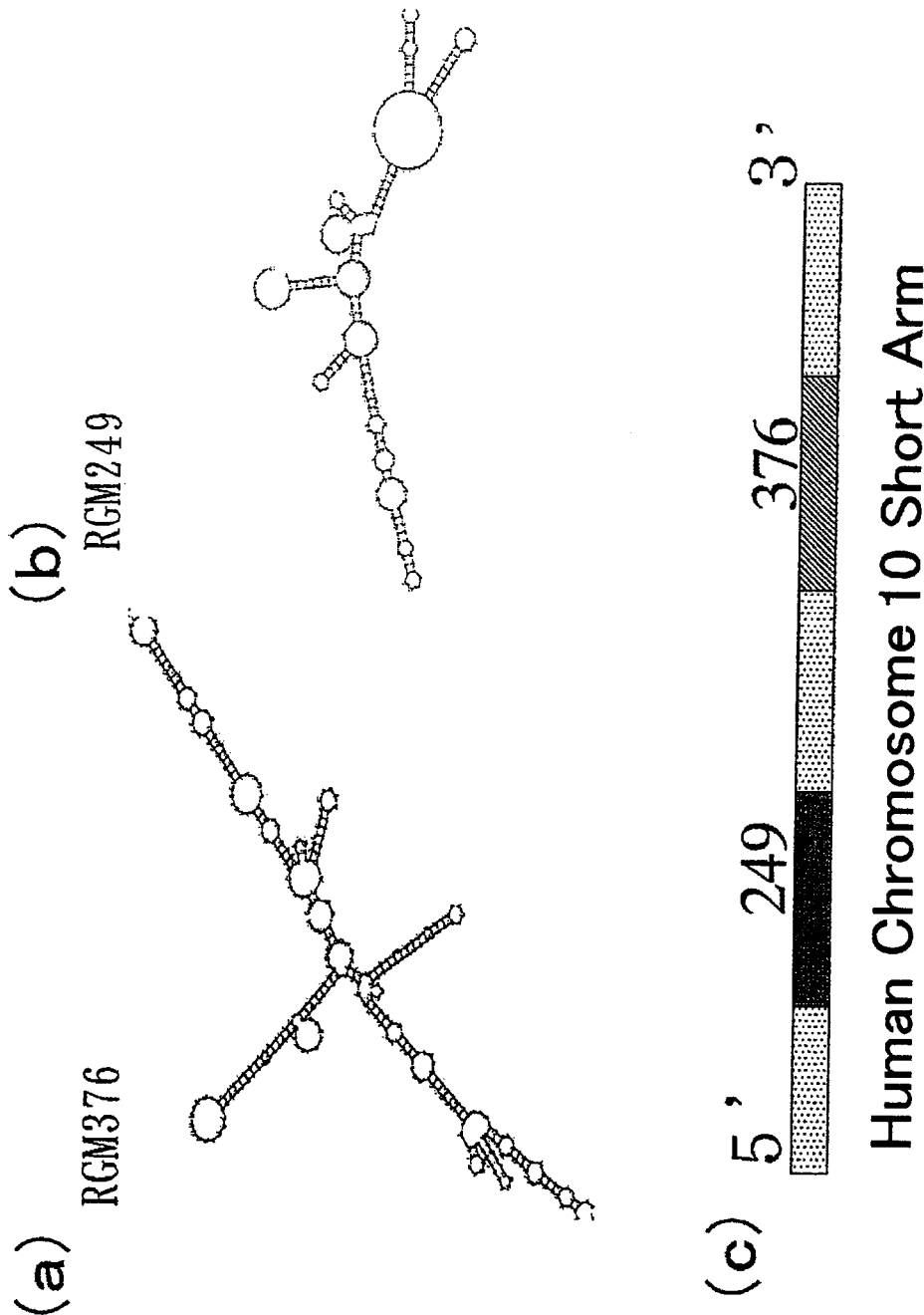

(a) RGM376 Base Sequence (SEQ ID No.1)
ACATTGCCTCCGGAAATAGACCCTCCCATATGTCAAGAATTGGGATGCTGACAT
ATGTGAGGAGGGCATGAACAACTGTTTCCCTGGGGTCAAATTGAAACCTGGGC
ATGTGGTGACAACACAATTACTTCAAGTCATCTCCACTGTGACAGAGGAATGA
GCACAAGAGAAGGGCGAGATGTCTAGAGATCAAGTGACCAGTATTAATCACAA
TGCTGACAACAGCGATTGTAAAGATTGCAGAATTGGCTGGCAGCTTCAGAAGG
CCTGAGAGCATGTACACAAGAGAAGAGTTAATGGAAGACCATGAATGTCCCAT
GCAGACCACACGTGGGCGAGCAGCAGTCTCCATGGCATATTTGATCTTGCAAA
GCAG (b) RGM249 Base Sequence (SEQ ID No.2)
GGAAAACTAAAATGAGAGAATGGGTGTCCAAGAGGACAAGTTCATGCTCACCC
GGTGATGAGAGTTTGATTGCAGAATAAGGCTAGACAAAGGGAAGCTGAACATG
ACCAAAGCCATGTGACATCGTATGATCCTCGAATCTCACAGTATCTATGTATCTA
TAATCAGATACATCCCTAGACTTTCCAGGAATTCTGGTACTTCACGAGGATGTG
AGAAGACTCTGAACAAAATAATACACTGCTCGTG (c) RGM376RNA Base Sequence (SEQ ID No.3)
ACAUUGCCUCCGGAAAUAGACCCUCCCAUAUGUCAAGAAUUGGGAUGCUGA
CAUAUGUGAGGAGGGCAUGAACAACUGUUUCCCUGGGGUCAAAUUGAAAC
CUGGGCAUGUGGUGACAACACAAUUACUUCAAGUCAUCUCCACUGUGACAG
AGGAAUGAGCACAAGAGAAGGGCGAGAUGUCUAGAGAUCAAGUGACCAGUA
UUAAUCACAAUGCUGACAACAGCGAUUGUAAAGAUUGCAGAAUUGGCUGG
CAGCUUCAGAAGGCCUGAGAGCAUGUACACAAGAGAAGAGUUAAUGGAAGA
CCAUGAAUGUCCCAUGCAGACCACACGUGGGCGAGCAGCAGUCUCCAUGGC
AUAUUUGAUCUUGCAAAGCAG (d) RGM249RNA Base Sequence (SEQ ID No.4)
GGAAAACUAAAAUGAGAGAAUGGGUGUCCAAGAGGACAAGUUCAUGCUCAC
CCGGUGAUGAGAGUUUGAUUGCAGAAUAAGGCUAGACAAAGGGAAGCUGA
ACAUGACCAAAGCCAUGUGACAUCGUAUGAUCCUCGAAUCUCACAGUAUCU
AUGUAUCUAUAAUCAGAUACAUCCCUAGACUUUCCAGGAAUUCUGGUACU
UCACGAGGAUGUGAGAAGACUCUGAACAAAAUAAUACACUGCUCGUG 376: (Seq. ID No. 1)
ACATTGCCTCCGGAAATAGACCCTCCCATATGTCAAGAATTGGGATGCTGACATATGTGAGGAG

GGCATGAACAACTGTTTCCCTGGGGTCAAATTGAAACCTGGGCATGTGGTGACAACACAATTAC

TTCAAGTCATCTCCACTGTGACAGAGGAATGAGCACAAGAGAAGGGCGAGATGTCTAGAGATC

AAGTGACCAGTATTAATCACAATGCTGACAACAGCGATTGTAAAGATTGCAGAATTGGCTGGCA

GCTTCAGAAGGCCTGAGAGCATGTAC[A]CAAGAGAAGAGTTAATGGAAGACCATGAATGTCCCA

TGCAGACCACACGTGGGCGAGCAGCAGTCTCCATGGCATATTTGATCTTGCAAAGCAG fig 6

(a) RGM376siRNA

A gcacaagagaagggcgagatgtcta(Seq. ID. No. 5)

GCACAAGAGAAGGGCGAGAUGUCUA(sense RNA sequence 5'- 3')(Seq. ID. No. 6)

UAGACAUCUCGCCCUUCUCUUGUGC(antisense RNA sequence 5'-3')(Seq. ID. No. 7)

B tccatggcatatttgatcttgcaaa(Seq. ID. No. 8)

UCCAUGGCAUAUUUGAUCUUGCAAA(sense RNA sequence 5'-3')(Seq. ID. No. 9)

UUUGCAAGAUCAAAUAUGCCAUGGA(antisense sequence 5'-3')(Seq. ID. No. 10)

(b)   7     CCUCCGGAAAUAGACCCUCCCAUAU(Seq. ID. No. 11)
    47    GCUGACAUAUGUGAGGAGGGCAUGA(Seq. ID. No. 12)
   147   UGACAGAGGAAUGAGCACAAGAGAA(Seq. ID. No. 13)
   161   GCACAAGAGAAGGGCGAGAUGUCUA(Seq. ID. No. 6)   ----- A
   166   AGAGAAGGGCGAGAUGUCUAGAGAU(Seq. ID. No. 14)
   169   GAAGGGCGAGAUGUCUAGAGAUCAA(Seq. ID. No. 15)
   173   GGCGAGAUGUCUAGAGAUCAAGUGA(Seq. ID. No. 16)
   176   GAGAUGUCUAGAGAUCAAGUGACCA(Seq. ID. No. 17)
   180   UGUCUAGAGAUCAAGUGACCAGUAU(Seq. ID. No. 18)
   181   GUCUAGAGAUCAAGUGACCAGUAUU(Seq. ID. No. 19)

(c) RGM376:
ACATTGCCTCCGGAAATAGACCCTCCCATATGTCAAGAATTGGGATGCTGACATATG

TGAGGAGGGCATGAACAACTGTTTCCCTGGGGTCAAATTGAAACCTGGGCATGTG

GTGACAACACAATTACTTCAAGTCATCTCCACTGTGACAGAGGAATGA<u>GCACAAGA</u>

<u>GAAGGGCGAGATGTCTA</u>GAGATCAAGTGACCAGTATTAATCACAATGCTGACAACA
     A

GCGATTGTAAAGATTGCAGAATTGGCTGGCAGCTTCAGAAGGCCTGAGAGCATGTA

CACAAGAGAAGAGTTAATGGAAGACCATGAATGTCCCATGCAGACCACACGTGGG

CGAGCAGCAGTCT<u>CCATGGCATATTTGATCTTGCAAA</u>GCAG(Seq. ID. No. 1)
                B (a) RGM 249 siRNA

① siRNA_72:
   GCAGAAUAAGGCUAGACAAAGGGAA(sense RNA sequence 5'-3')(Seq. ID No. 20)
   UUCCCUUUGUCUAGCCUUAUUCUGC(antisense RNA sequence 5'-3')(Seq. ID No. 21)

② siRNA_125:
   GUAUGAUCCUCGAAUCUCACAGUAU(sense RNA sequence 5'-3')(Seq. ID No. 22)
   AUACUGUGAGAUUCGAGGAUCAUAC(antisense RNA sequence 5'-3')(Seq. ID No. 23)

(b)
| | | |
|---|---|---|
| 60 | GAGAGUUUGAUUGCAGAAUAAGGCU | (Seq. ID No. 24) |
| 66 | UUGAUUGCAGAAUAAGGCUAGACAA | (Seq. ID No. 25) |
| 67 | UGAUUGCAGAAUAAGGCUAGACAAA | (Seq. ID No. 26) |
| 72 | GCAGAAUAAGGCUAGACAAAGGGAA | (Seq. ID No. 20) ① |
| 78 | UAAGGCUAGACAAAGGGAAGCUGAA | (Seq. ID No. 27) |
| 116 | AUGUGACAUCGUAUGAUCCUCGAAU | (Seq. ID No. 28) |
| 118 | GUGACAUCGUAUGAUCCUCGAAUCU | (Seq. ID No. 29) |
| 120 | GACAUCGUAUGAUCCUCGAAUCUCA | (Seq. ID No. 30) |
| 124 | UCGUAUGAUCCUCGAAUCUCACAGU | (Seq. ID No. 31) |
| 125 | CGUAUGAUCCUCGAAUCUCACAGUA | (Seq. ID No. 32) ②' |

(c) RGM249

GGAAAACTAAAATGAGAGAATGGGTGTCCAAGAGGACAAGTTCATGCTCACCCGG

TGATGAGAGTTTGATT<u>GCAGAATAAGGCTAGACAAAGGGAA</u>GCTGAACATGACCAA
                                            ①

AGCCATGTGACATC<u>GTATGATCCTCGAATCTCACAGTAT</u>CTATGTATCTATAATCAG
                              ②

ATACATCCCTAGACTTTCCAGGAATTCTGGTACTTCACGAGGATGTGAGAAGACTC

TGAACAAAATAATACACTGCTCGTG(Seq. ID No. 2)

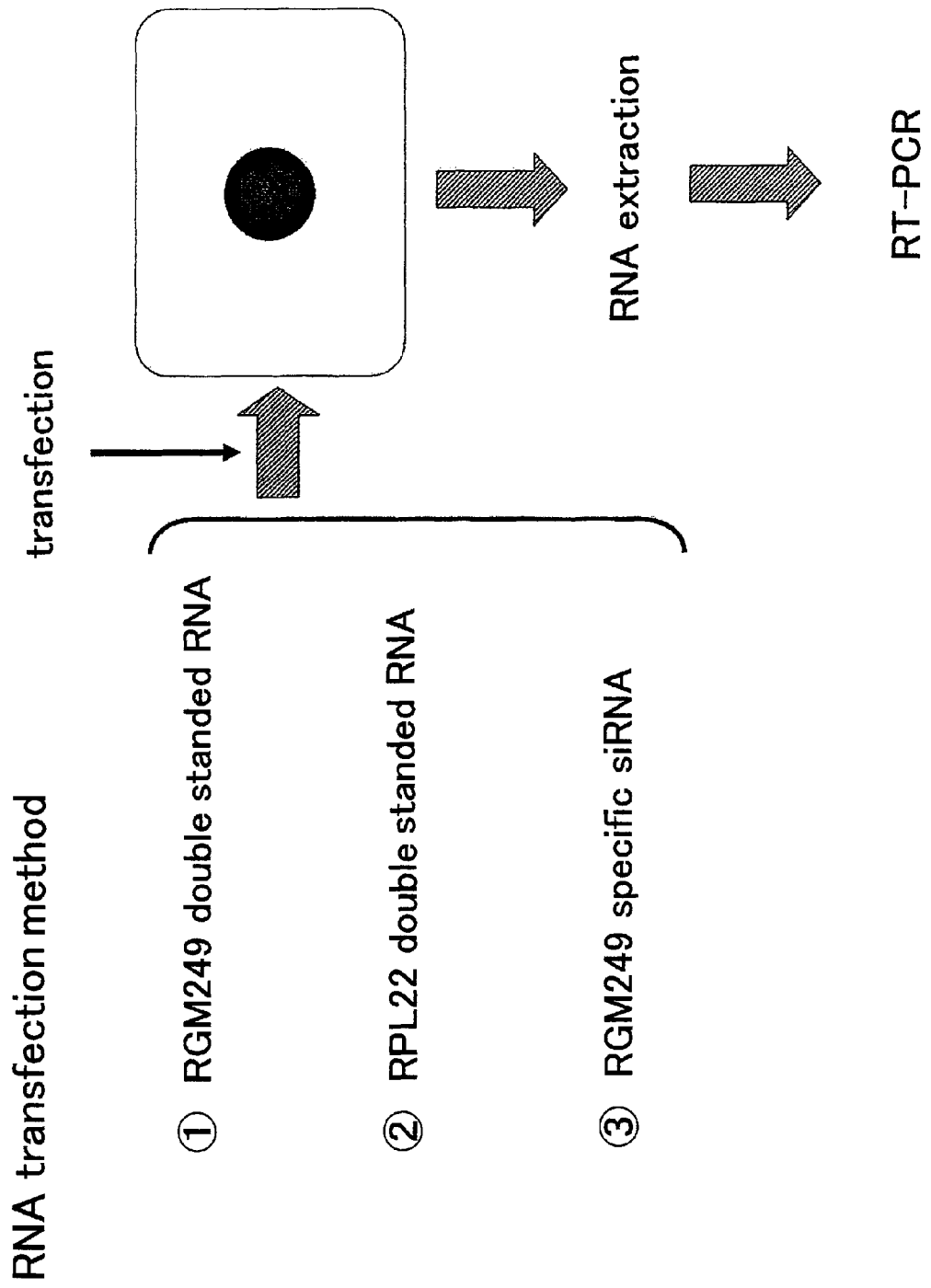

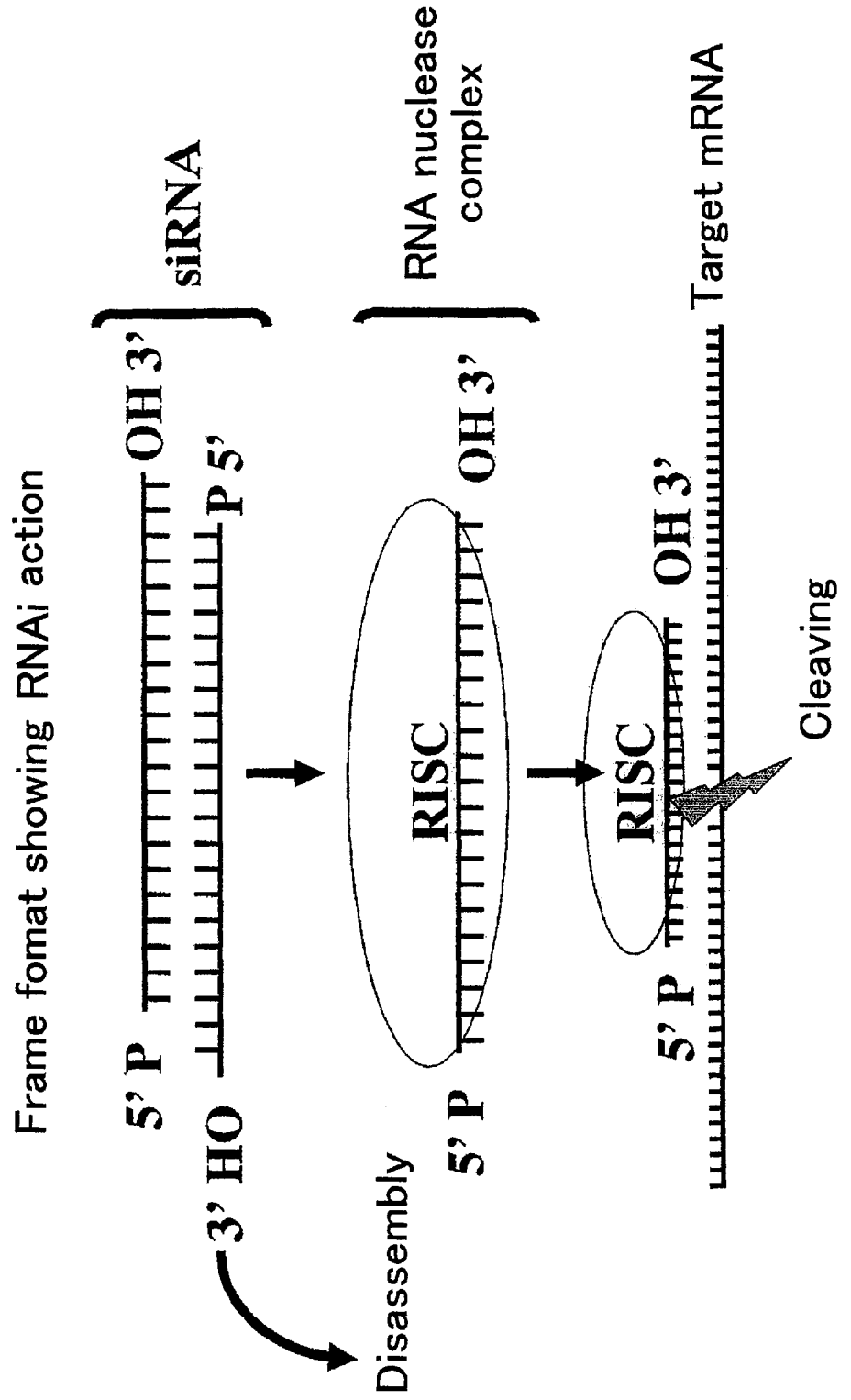

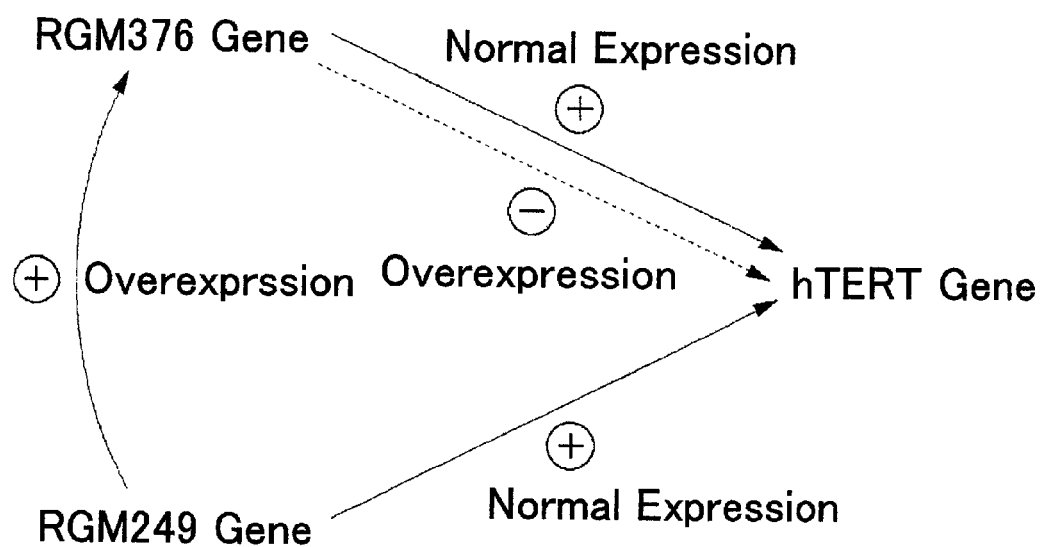

(a) Top strand oligo

Sense target sequence     Loop     Antisense target sequence

5'-CACCGCAGAATAAGGCTAGACAAAGCGAACTTTGTCTAGCCTTATTCTGC-3'

Sequence required for cloning (Seq. ID No. 33)

(b) Bottom strand oligo

Reverse complement of top strand oligo sequence

5'-AAAAGCAGAATAAGGCTAGACAAAGTTCGCTTTGTCTAGCCTTATTCTGC-3'

Sequence required for cloning (Seq. ID No. 34)

↓ Annealing (c)

5'-CACCGCAGAATAAGGCTAGACAAAGCGAACTTTGTCTAGCCTTATTCTGC-3'
    CGTCTTATTCCGATCTGTTTCGCTTGAAACAGATCGGAATAAGACGAAAA-3'

Mutation1 Top strand oligo

```
                   Sense target sequence          Loop       Antisense target sequence
5'-CACCGCAGAATAAGGCTAGACAAAGGCGAACTTTGTCTAGCCTTATTCTGC-3'
   └─────────┘
   Sequense required           ↓ deletion
   for cloning
                        CTTTGTC AGCCTTATTCTGC
                                              (Seq. ID No. 35)
```

Mutation1 Bottom strand oligo

```
                   Reverse complement of top strand oligo sequence
5'-AAAAGCAGAATAAGGCTAGACAAAGTTCGCTTTGTCTAGCCTTATTCTGC-3'
   └─────────┘
   Sequense required           ↓ deletion
   for cloning
                        GCAGAATAAGGCT GACAAA
                                              (Seq. ID No. 36)
```

HTERT GENE EXPRESSION REGULATORY GENE

SEQUENCE LISTING

This patent application incorporates by reference the attached Sequence Listing.

TECHNICAL FIELD

The present invention concerns an hTERT expression regulatory gene.

Regarding the enzyme telomerase that is thought to play an extremely important role in the mechanism of carcinogenesis, it is known that the telomerase reverse transcriptase gene (hTERT) and RNA tape (hTR) are the main regulatory factors for telomerase enzyme expression, and a great amount of research is being done. However, a direct mechanism linking telomerase expression and carcinogenesis has yet to be made clear. It can be anticipated that a large number of factors within the genome are involved, but the mechanism for telomerase activation is complex, and it is expected that further unknown factors exist.

Additionally, after the year 2000, the role of small RNA called microRNA (miRNA) has been attracting attention, and the elucidation of its role has given rise to international competition that is unprecedented in its intensity. Especially noteworthy is that although miRNA plays an important role in determining the fate of human cells, the RNA genes and the miRNA thereof involved in carcinogenesis (particularly telomerase) is not known for human cells.

Additionally, RNA interference (RNAi) has been garnering attention as an efficient technology that blocks the expression of a specific gene. By using RNAi technology, researchers can control the expression of genes that they want to study. Whereby, the cell phenotype in a state where this gene is not expressed can be examined, and the gene function can be analyzed.

At first, it became clear that RNAi is a powerful method for reducing the expression of a specific gene, by transfecting long double-stranded DNA into invertebrates such as *Drosophila* and *C. elegans*. At present, eukaryotic cells including mammalian cells can be analyzed utilizing an improved RNAi knockdown method.

As a conventional RNAi technology, for example, there is that described in Japanese Unexamined Patent Publication (Kohyo) No. 2002-516062. In this RNAi technology, target gene inactivation is performed with double-stranded RNA comprising RNA with a sequence homologous to the targeted gene and its complementary chain. Further, this document describes that it is necessary for the RNA sequence used to be at least 50 bases long. Additionally, the experimental examples described in this citation use nematodes.

Additionally, as a conventional RNAi technology, there is, for example, that described in Japanese Unexamined Patent Publication (Kohyo) No. 2003-529374. This RNAi technology uses siRNA in order to induce RNAi. This document describes (1) structural features of the siRNA, (2) a method for generating siRNA of approximately 21-23 bases in *drosophila* embryo extract having RNAi activity (using Dicer activity therein), (3) chemical synthesis of siRNA, and (4) transfecting and keeping siRNA in a cell or individual animal.

Additionally, as a conventional RNAi technology, there is that described in SAYDA M. ELBASHIR, JENS HARBORTH, WINFRIED LENDECKEL, ABDULLAH YALCIN, KLAUS WEBER, and THOMAS TUSCHL, "Duplexes of 21-nucleotide RNAs mediate RNA interference in cultured mammalian cells", *Nature,* 24 May 2001, Vol. 411, pp. 494-498. This document recites that by directly transfecting siRNA that has been cut into short pieces with Dicer into mammalian cells, the RNAi pathway can be made to operate without activation of the interferon pathway.

Additionally, as a conventional RNAi technology, there is, for example, that described in Jurgen Soutschek, Akin Akinc, Birgit Bramlage, Klaus Charisse, Rainer Constien, Mary Donoghue, Sayda Elbashir, Anke Geick, Philipp Hadwiger, Jens Harborth, Matthias John, Venkitasamy Kesavan, Gary Lavine, Rajendra K. Pandey, Timothy Racie, Kallanthottathi G. Rajeev, Ingo Rohl, Ivanka Toudjarska, Gang Wang, Silvio Wuschko, David Bumcrot, Victor Koteliansky, Stefan Limmer, Muthiah Manoharan, and Hans-Peter Vornlocher, "Therapeutic silencing of an endogenous gene by systemic administration of modified siRNAs", *Nature,* 11 Nov. 2004, Vol. 432, pp. 173-178. This document describes that siRNAs that were linked to cholesterol sustainedly suppressed the expression of a gene encoding apoB.

Additionally, as a conventional art for suppressing telomerase activity, there is, for example, that described in Japanese Unexamined Patent Publication (Kokai) No. 2002-104995. This document describes a medicine comprising a combination of a vitamin D receptor agonist such as 1,25-dihydroxyvitamin D3 and a retinoid X receptor (RXR) ligand such as 9-cis retinoic acid. Additionally, according to this document, this medicine is a substance that can act directly or indirectly on the human telomerase reverse transcriptase (hTERT) promoter region, and reduce the degree of its expression, and is a medicine that is useful as a telomerase activation suppressor and an anti-cancer drug.

Additionally, as a conventional art for suppressing telomerase activity, for example, there is that described in Japanese Unexamined Patent Publication (Kokai) No. 2004-350607. This document describes a double stranded polynucleotide showing an RNA interference effect against the human telomerase reverse transcriptase gene. This document describes that this double stranded polynucleotide is designed based upon the human telomerase reverse transcriptase gene sequence, and it inhibits the expression of the human telomerase reverse transcriptase gene.

Additionally, as a conventional art for suppressing telomerase activation, there is, for example, that described in the specification of U.S. Patent Application No. 2003/0099616. This document describes a dual specificity tumor killing vector driven by the telomerase promoter. Additionally, this document describes that this expression vector that operates due to the telomerase promoter can target tumor cells, and can be used for RNAi.

However, the conventional art described in the above-mentioned documents have room for improvement on the following points. First, with the abovementioned conventional art described in Patent Citation 3 and Patent Citation 4, there is room for improvement with regard to the suppression of telomerase activity. Most of all, since telomerase is a large molecule of approximately 4.0 kb, human control thereof is difficult, so there is room for further improvement with regard to the efficiency of telomerase activity suppression and stability.

Second, for the abovementioned conventional art described in Patent Citation 1, Patent Citation 2, Patent Citation 5, Non-Patent Citation 1, and Non-Patent Citation 2, whereas the development of areas having to do with methods for designing and administering drug candidate substances that are useful for anti-cancer suppression is advancing, the discovery of a raw sample that can be a design source for such drug candidate substances has been delayed. That is, since reports of novel factors and mechanisms concerning activation of telomerase are scarce (particularly activation of expression of the telomerase reverse transcriptase gene), the raw samples that can be a design source for a drug candidate substances are in short supply, so there is room for further improvement with regard to the degree of freedom of design of drug candidate substances that suppress telomerase activity.

DISCLOSURE OF THE INVENTION

The present invention was made in view of the abovementioned circumstances, and has the aim of providing a novel substance that regulates the expression of telomerase reverse transcriptase within a mammalian cell.

According to the present invention, an hTERT expression regulatory gene comprising the base sequence shown in SEQ ID No. 1 is provided.

If the expression of this gene comprising the base sequence shown in SEQ ID No. 1 is inhibited, the expression of telomerase reverse transcriptase is suppressed. Additionally, if this gene comprising the base sequence shown in SEQ ID No. 1 is overexpressed, the expression of telomerase reverse transcriptase is suppressed. Therefore, according to this constitution, the expression of telomerase reverse transcriptase can be regulated.

Additionally, according to the present invention, products of hTERT expression regulatory RNA comprising the base sequence shown in SEQ ID No. 3 and the like are provided.

If the expression of this hTERT expression regulatory RNA comprising the base sequence shown in SEQ ID No. 3 is suppressed, the expression of telomerase reverse transcriptase is suppressed. Additionally, if this hTERT expression regulatory RNA comprising the base sequence shown in SEQ ID No. 3 is overexpressed, the expression of telomerase reverse transcriptase is suppressed. Whereby, according to this constitution, the expression of telomerase reverse transcriptase can be regulated.

Further, since the description given above may seem prima facie to be inconsistent, an explanation shall be provided below in order to avoid misunderstanding. FIG. 27 is a conceptual diagram summarizing the mutual control relationship predicted for the RGM376 gene (SEQ ID No. 1), the RGM249 gene (SEQ ID No. 3), and the hTERT gene. In FIG. 27, + indicates promotion, whereas – indicates suppression. That is, as can be seen from the experimental data from the below-described Embodiment 1 and Embodiment 2, the RGM 376 gene (SEQ ID No. 1) promotes the expression of the hTERT gene when at a normal level of expression, but if overexpressed, it suppresses the expression of the hTERT gene. Because of this, the expression of the hTERT gene will be suppressed whether the expression of the RGM376 gene (SEQ ID No. 1) is inhibited, or whether it is overexpressed.

Additionally, as can be seen from the experimental data from the below-described Embodiment 1 and Embodiment 2, the RGM249 gene (SEQ ID No. 3) promotes the expression of the hTERT gene when at a normal level of expression. On the other hand, it suggests that the RGM249 gene (SEQ ID No. 3), when overexpressed, promotes the expression of the RGM376 gene (SEQ ID No. 1) and makes the RGM376 gene (SEQ ID No. 1) be overexpressed (data not shown). Therefore, it can be supposed that if the RGM249 gene (SEQ ID No. 3) is overexpressed, the expression of the hTERT gene will be suppressed as a result. Therefore, it can be supposed that the expression of the hTERT gene (SEQ ID No. 3) is suppressed whether the expression of the RGM249 gene (SEQ ID No. 3) is inhibited, or whether it is overexpressed.

Additionally, according to the present invention, a double stranded RNA is provided that includes a first base sequence with a length of 15 bases or longer and 30 bases or shorter, that corresponds to one portion of the abovementioned hTERT expression regulatory RNA, and a second base sequence with a length of 15 bases or longer and 30 bases or shorter that is complementary to this first base sequence.

This double stranded RNA suppresses the expression of the abovementioned hTERT expression regulatory RNA. Additionally, if the expression of the abovementioned hTERT expression regulatory RNA is suppressed, the expression of the telomerase reverse transcriptase gene is suppressed. Whereby, according to this constitution, the expression of the telomerase reverse transcriptase gene can be regulated.

Further, the first base sequence may have a length of 18 or more bases and 25 or less bases. Additionally, the second base sequence may also have a length of 18 or more bases and 25 or fewer bases. This is because any double-stranded RNA containing a base sequence with a length within this range has its function as siRNA or miRNA improved.

Additionally, the present invention also provides single stranded RNA including a first base sequence having a length of 15 or more bases and 30 or fewer bases, corresponding to one portion of the hTERT expression regulatory RNA, and a second base sequence having a length of 15 or more bases and 30 or fewer bases disposed in a direction opposite to that of the first base sequence, and complementary to the first base sequence.

This single-stranded RNA suppresses the expression of the abovementioned hTERT expression regulatory RNA. Additionally, if the expression of the abovementioned hTERT expression regulatory RNA is suppressed, the expression of the telomerase reverse transcriptase gene is suppressed. Whereby, according to this constitution, the expression of the telomerase reverse transcriptase gene can be regulated.

Further, the first base sequence can have a length of 18 or more bases and 25 or fewer bases. Additionally, the second base sequence can also have a length of 18 or more bases and 25 or fewer bases. This is because any single-stranded RNA containing a base sequence with a length within this range has its function as shRNA improved.

Additionally, the present invention also provides RNA that contains a plurality of types of double stranded RNA that are produced by cleaving, with a micro RNA maturation enzyme, double stranded RNA including the abovementioned hTERT expression regulatory RNA and RNA containing a base sequence complementary to that of this hTERT expression regulatory RNA. Further, examples of micro RNA maturation enzymes are enzymes that are involved in the maturation of micro RNA, such as Drosha and Dicer.

This RNA, including a plurality of types of double stranded RNA, suppresses the expression of the abovementioned hTERT expression regulatory RNA. Additionally, if the expression of the abovementioned hTERT expression regulatory RNA is suppressed, the expression of telomerase reverse transcriptase is also suppressed. Whereby, according to this constitution, the expression of telomerase reverse transcriptase can be regulated.

Additionally, the present invention provides an hTERT expression regulatory gene comprising the base sequence shown in SEQ ID No. 2.

If the expression of this gene comprising the base sequence shown in this SEQ ID No. 2 is inhibited, the expression of the telomerase reverse transcriptase gene is suppressed. Whereby, according to this constitution, the expression of the telomerase reverse transcriptase gene can be regulated.

Additionally, the present invention provides an hTERT expression regulatory RNA comprising the base sequence shown in SEQ ID No. 4.

If the expression of this hTERT expression regulatory gene comprising the base sequence shown in this SEQ ID No. 4 is suppressed, the expression of the telomerase reverse transcriptase gene is suppressed. Whereby, according to this constitution, the expression of the telomerase reverse transcriptase gene can be regulated.

Additionally, the present invention provides a double stranded RNA that includes a first base sequence with a length of 15 bases or longer and 30 bases or shorter, that corresponds to one portion of the abovementioned hTERT expression regulatory RNA, and a second base sequence with a length of 15 bases or longer and 30 bases or shorter that is complementary to this first base sequence.

This double stranded RNA suppresses the expression of the abovementioned hTERT expression regulatory RNA. Additionally, if the expression of the abovementioned hTERT expression regulatory RNA is suppressed, the expression of the telomerase reverse transcriptase gene is suppressed. Whereby, according to this constitution, the expression of the telomerase reverse transcriptase gene can be regulated.

Further, the first base sequence can have a length of 18 or more bases and 25 or fewer bases. Additionally, the second base sequence can also have a length of 18 or more bases and 25 or fewer bases. This is because any double stranded RNA containing a base sequence with a length within this range has its function as siRNA or miRNA improved.

Additionally, the present invention also provides single stranded RNA including a first base sequence having a length of 15 or more bases and 30 or fewer bases, corresponding to one portion of the abovementioned hTERT expression regulatory RNA, and a second base sequence having a length of 15 or more bases and 30 or fewer bases disposed in a direction opposite to that of the first base sequence, and complementary to the first base sequence.

This single stranded RNA suppresses the expression of the abovementioned hTERT expression regulatory RNA. Additionally, if the expression of the abovementioned hTERT expression regulatory RNA is suppressed, the expression of the telomerase reverse transcriptase gene is suppressed. Whereby, according to this constitution, the expression of the telomerase reverse transcriptase gene can be regulated.

Further, the first base sequence can have a length of 18 or more bases and 25 or fewer bases. Additionally, the second base sequence can also have a length of 18 or more bases and 25 or fewer bases. This is because any single stranded RNA containing a base sequence with a length within this range has its function as shRNA improved.

Additionally, the present invention also provides RNA that contains a plurality of types of double stranded RNA that are produced by cleaving, with a micro RNA matureation enzyme, double stranded RNA including the abovementioned hTERT expression regulatory RNA and RNA containing a base sequence complementary to that of this hTERT expression regulatory RNA. Further, examples of micro RNA maturation enzymes are enzymes that are involved in the maturation of micro RNA, such as Drosha, Dicer, Ago2, and TRBP.

This RNA including a plurality of types of double stranded RNA suppresses the expression of the abovementioned hTERT expression regulatory RNA. Additionally, if the expression of the abovementioned hTERT expression regulatory RNA is suppressed, the expression of telomerase reverse transcriptase is also suppressed. Whereby, according to this constitution, the expression of telomerase reverse transcriptase can be regulated.

Further, the abovementioned phenomena are all phenomena occurring within mammalian cells.

Additionally, the abovementioned genes and RNA are not limited to the abovementioned base sequences, but genes and RNA comprising base sequences wherein one or a few of the bases in these base sequences are missing or replaced, or are added to, also have similar effects.

Additionally, the abovementioned genes and RNA are not limited to the abovementioned base sequences, and genes and RNA comprising base sequences of mammal-derived polynucleotide molecules that hybridize under stringent conditions to polynucleotide molecules comprising base sequences that are complementary to the polynucleotide molecules comprising these base sequences also have similar effects.

Additionally, the abovementioned genes and RNA are one mode of the present invention, and the genes and RNA of the present invention may be arbitrary combinations of the constituent elements given above. Additionally, vectors and complexes of the present invention also have a similar constitution, and have similar effects.

That is, according to the present invention, the expression of the telomerase reverse transcriptase gene within mammalian cells can be regulated because either one of two novel types of genes that regulate the expression of the telomerase reverse transcriptase gene, or substances obtainable based upon these genes are used.

BRIEF DESCRIPTION OF DRAWINGS

[FIG. 2] Conceptual diagram for explaining the procedure for cloning gene 1.

[FIG. 3] Conceptual diagram for explaining the location on human chromosome 10, and the structure of gene 2.

[FIG. 4] Conceptual diagram for explaining the structure and relative position of RNA that is a transcription product of gene 1 and gene 2.

[FIG. 5] Diagram for explaining the sequence of gene 1 and gene 2.

[FIG. 6] Diagram for explaining the sequence of a variant of gene 1.

[FIG. 7] Diagram for explaining the sequence of siRNA designed based upon gene 1.

[FIG. 8] Diagram for explaining the sequence of siRNA designed based upon gene 2.

[FIG. 9] Diagram for explaining method for transfecting RNA into a cell.

[FIG. 10] Frame format showing effect of RNAi.

[FIG. 27] Conceptual diagram summarizing expected mutual control relationship between RGM376 gene (SEQ ID No. 1), RGM249 gene (SEQ ID No. 3), and hTERT gene.

[FIG. 28] Diagram for explaining sequence of RGM249 shRNA to be designed based upon gene 2.

[FIG. 29] Diagram for explaining sequence of RGM249 variant shRNA to be designed based upon gene 2.

BEST MODE FOR EMBODYING THE INVENTION

Herebelow, a mode for embodying the present invention shall be explained using figures. In all of the figures, identical reference numbers shall be associated with identical constituent elements, and explanations shall be appropriately omitted.

<Explanation of Telomerase>

The present mode of embodiment concerns telomerase, an enzyme thought to play an extremely important role in the mechanism of carcinogenesis. In the present embodiments, a functional analysis shall be carried out of two RNA genes that are closely involved in, and control, the expression of telomerase reverse transcriptase (hTERT), which is the primary candidate for carcinogenesis, that is, a cancer antigen.

Telomerase is an enzyme that is needed for the elongation of the telomere sequences at the ends of chromosomes and the stability of chromosomes, and is deeply involved in escaping from cell aging, and the inducing of canceration.

Examples of molecules that are necessary for the formation of telomerase are hTERT (human telomerase reverse transcriptase), hTR (human telomerase RNA tape: RNA component), TEP1 (telomerase-associated protein 1), Dyskerin (DKC1), RPL22, Nola3, La-antigen, Staufen, and H/ACA, and the activation and generation of telomerase enzymes is controlled by these molecules.

<Position of the Two Genes on the Chromosome and the Background of Their Discovery>

Figure 1:
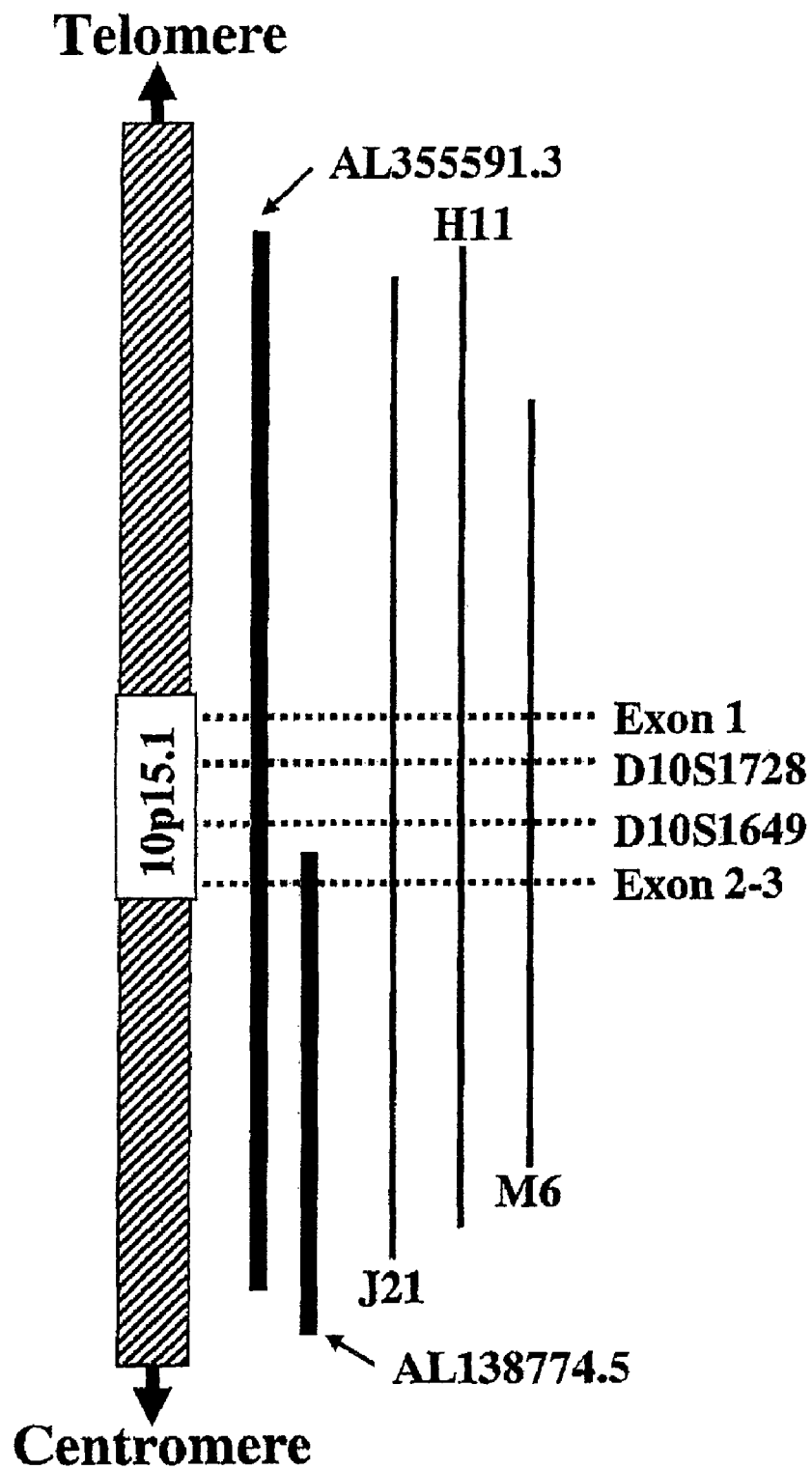
[FIG. 1] Physical map showing the position of gene 1 and gene 2 in the vicinity of band 15.1 on the short arm of human chromosome 10.

FIG. 1 is a physical map showing the position of gene 1 and gene 2 in the vicinity of band 15.1 on the short arm of human chromosome 10.

Both of the genes cloned from the short arm of human chromosome 10 by the present inventor as telomerase controlling genes are mapped on adjacent positions on approximately 1.5 kb on the genome. Further, in the diagram, on the chromosome shown on the left, the upper direction is the telomere direction, and the lower direction is the centromere direction.

Gene1 shows the location of gene 1, which the present inventor named RGM376. Additionally, Gene2 shows the location of gene 2, which the present inventor named RGM249. Further, between Gene1 and Gene2 exist DNA markers that are named D10S1728 and D10S1649.

Gene1, D10S1728, D10S1649, and Gene2 all exist in a common region with a length of 1.5 kb in the genome library, names AL355591.3, AL138774.5, J21, H11, and M6.

FIG. 2 is a conceptual diagram for explaining the procedure for cloning gene 1. The present inventor, in order to clone the RGM376 gene (gene 1), first performed exon trapping, after having performed the micro nuclear fusion method and BAC screening. Next, for the region narrowed down by exon trapping, the identification of an exon that suppresses telomerase activity and the expression of hTERT mRNA was performed by forced expression.

Then, as a result of an examination, ORF analysis, and in vitro translation of the base sequence of the identified exon of the RGM376 gene, it was strongly suggested that the RGM376 gene (gene 1) is an ncRNA that does not synthesize a protein.

Further, the RGM 249 gene (gene2) is a gene that was identified as an exon within a region of length 1.5 kb that is shared by a plurality of clones obtained during the cloning of the RGM376 gene (gene 1).

This RGM249 gene (gene 2) was also selected out as a gene that is expressed in cancer cell lines, from 44 exons obtained by exon trapping using a BAC library of the 10p14-15 region of the short arm of human chromosome 10, whereon the existence of a telomerase and cancer-related control gene was suggested, and cDNA was obtained.

As a result of having performed upon the identified RGM249 gene the analysis of the base sequence of its exons, and in vitro transcription and translation using protein expression vectors, it was strongly suggested that the RGM249 gene (gene 2) is an ncRNA that does not encode a protein.

<Explanation of Structure and Function of the Two Genes>

FIG. 3 is a conceptual diagram for explaining the location upon human chromosome 10 and the structure of gene 2. The RGM249 gene (gene2) exists at band 15.3 on the short arm of human chromosome 10. Additionally, the length of the RGM249 gene is 249 bp. Further, the RGM249 gene comprises two exons. One exon has a length of 190 bp, while the other exon has a length of 59 bp.

The RGM376 gene (gene 1) is also similarly located at band 15.3 on the short arm of human chromosome 10. Additionally, the length of the RGM376 gene is 376 bp.

FIG. 4 is a conceptual diagram for explaining the structure and relative position of the RNA that is a transcription product of gene 1 and gene 2. FIG. 4(a) shows the putative two-dimensional structure of the RNA that is a transcription product of the RGM376 gene. Additionally, FIG. 4(b) shows the putative two-dimensional structure of the RNA that is a transcription product of the RGM249 gene.

FIG. 4(c) shows the relative position of the RGM376 gene and the RGM249 gene on the short arm of human chromosome 10. From the fact that, in this way, the RGM249 gene is located upstream from the RGM376 gene, a mechanism that integrates and controls these genes can be supposed to exist, and the involvement of both genes in the mechanism of carcinogenesis is suggested.

One of these RNA genes, the RGM376 gene (gene 1), functions to suppress hTERT due to overexpression, and the other RNA gene, the RGM249 gene (gene 2), functions synchronously with hTERT expression.

More specifically, as shall be described below, there are two of these RNA genes, one that is expressed in liver cancer and behaves in unison with the expression of hTERT (gene 2), and one that is expressed in liver cells, and functions suppressively against cancer cells (gene 1), and they have functions that are mutually conflicting. Additionally, as shall be described below, the former (gene 2), after suppressing the telomerase gene with dsRNA, causes the cell death of cancer cells, and the latter (gene 1) acts suppressively against liver cancer, lung cancer, breast cancer, and the like by forced expression.

Additionally, from FIG. 4(a) and FIG. 4(b), there is the possibility that by dicing with enzymes such as Drosha and Dicer, miRNA is produced within living organisms from this RNA. In actuality, as described below, miRNA cluster genes (gene 1 and gene 2) that have been cloned from the short arm of human chromosome 10, as telomerase control genes, produce miRNA of 20 mer to 60-70 mer by the action of enzymes such as Drosha and Dicer. Experimental data also strongly suggests that in this way, micro RNA is produced, and it is involved in control. Further, by designing and constructing small functional RNA such as these miRNA, application to highly specific anti-cancer genetic medicine can be expected.

FIG. 5 is a diagram for explaining the sequence of gene 1 and gene 2. FIG. 5(a) shows the base sequence of the RGM376 gene (gene 1). The RGM376 gene has a length of 376 bases. Additionally, FIG. 5(b) shows the base sequence of the RGM249 gene (gene 2). The RGM249 gene has a length of 249 bases.

FIG. 5(c) shows the base sequence of the RNA that is the transcription product of the RGM 376 gene (gene 1). The RNA that is a transcription product of the RGM376 gene has a length of 376 bases. Additionally, FIG. 5(d) shows the base sequence of the RNA that is a transcription product of the RGM249 gene (gene 2). The RNA that is the transcription product of the RGM249 gene has a length of 249 bases.

FIG. 6 is a diagram for explaining the sequence of a variant of gene 1. As the result of transfecting an RGM376 variant wherein the mutation was induced by Mutazyme, a clone having a mutation at one base (A) that corresponds to the 280th base from the 5' end (muta 376-3-1-2) showed weak growth suppression and telomerase expression suppression (suppression of mRNA expression and suppression of telomerase activity).

That is, a gene comprising a base sequence wherein one or a plurality of bases from the base sequence of the RGM376 gene (gene 1) are missing, replaced, or added to, also shows telomerase expression suppression (suppression of mRNA expression and suppression of telomerase activity), similarly to gene 1.

Additionally, it is expected that a gene comprising a base sequence of mammal-derived DNA molecules that hybridize under stringent conditions to DNA molecules comprising a base sequence that is complementary to the RGM 376 gene (gene 1), also shows suppression of telomerase expression, similarly to gene 1.

Additionally, regarding the RGM249 gene (gene 2) also, it is expected that a gene comprising a base sequence wherein one or a plurality of the bases of the base sequence of gene 2 are missing, replaced, or added to, will also function as an hTERT expression regulatory gene that synchronizes with the expression of hTERT, similarly to gene 2.

Further, it is expected that a gene comprising a base sequence of mammal-derived DNA molecules that hybridize under stringent conditions to DNA molecules comprising a base sequence that is complementary to gene 2, will also function as an hTERT expression regulatory gene that synchronizes with the expression of hTERT, similarly to gene 2.

Additionally, regarding the RNA that are transcription products of gene 1 and gene 2, RNA that comprises base sequences wherein one or a plurality of bases are missing, replaced, or added to the original RNA, are expected to have a similar function to the original RNA.

Further, regarding RNA that is a transcription product of gene 1 or gene 2 also, mammal-derived RNA that hybridizes under stringent conditions to RNA molecules comprising base sequences that are complementary to these original RNA molecules is expected to have a function similar to the original RNA.

FIG. 7 is a diagram for explaining the sequence of siRNA designed based upon gene 1. FIG. 7(a), A and B are diagrams that show an example of a double strand (sense strand and antisense strand) of siRNA designed based upon the RGM376 gene (gene 1). As described below, this double-stranded siRNA shown in A and B suppresses the expression of the RNA of the RGM376 gene (gene 1).

FIG. 7(b) is a diagram that shows a plurality of examples of sense strands of siRNA designed by Invitrogen (registered trademark) BLOCK-iT RNAi Designer, manufactured by Invitrogen Corporation, based upon the RGM376 gene (gene 1). Among these sense strands of siRNA, the sense strand of SEQ ID No. 6 corresponds to FIG. 7(a) A.

More specifically, the design of chemically modified siRNA was carried out using Stealth (registered trademark) RNAi Designer. FIG. 7(b) lists, among the results of function prediction using Stealth RNAi Designer, those that have a high predicted value for functioning as an siRNA. The details of chemical modification by Stealth RNAi have not been made publicly available, since they are an industrial secret, but they are obtainable upon ordering from Invitrogen Corporation.

It is expected that any double stranded siRNA whereof the sense strand is a sequence listed in FIG. 7(b), suppresses the expression of the RNA of the RGM376 gene (gene 1), similarly to the siRNA of FIG. 7(a), A and B.

Further, the double stranded siRNA can be Stealth RNAi, but it is not particularly restricted, and can have overhangs with a length of two bases on the 3' end of both the sense strand and the antisense strand. Additionally, these RNA can be not only double stranded siRNA, but also single stranded shRNA wherein a hairpin loop sequence with a length of 4 bases or more is disposed in between a sense sequence (corresponding to the sense strand) and an antisense sequence (corresponding to the antisense strand). Further, there is no particular limit on the length of this hairpin loop sequence, but it can be, for example, 8 bases long. This is because it is expected that any of these will suppress the expression of the RNA of the RGM376 gene (gene 1).

FIG. 7(c) is a diagram showing the location on the entire length of the sequence of the RGM376 gene (gene 1) that corresponds to the sequence of the sense strand of FIG. 7(a) A and B. The underlined portions indicated by the reference letters A and B correspond to the sequences of the sense strands of A and B.

FIG. 8 is a diagram for explaining the sequence of siRNA that is designed based upon gene 2. FIG. 8(a), (1) (the number is circled in the diagram) and (2) (the number is circled in the diagram) are diagrams that show an example of a double strand (sense strand and antisense strand) of siRNA designed based upon the RGM249 gene (gene 2). As described below, this double stranded siRNA shown in (1) and (2) suppresses the expression of the RNA of the RGM249 gene (gene 2).

FIG. 8(b) is a diagram that shows a plurality of examples of sense strands of siRNA designed by Invitrogen (registered trademark) BLOCK-iT RNAi Designer, manufactured by Invitrogen Corporation, based upon the RGM249 gene (gene 2). Among the sense strands of these siRNA, the sense strand of SEQ ID No. 20 corresponds to FIG. 7(a) (1) (the number is circled in the diagram). Additionally, the sense strand of SEQ ID No. 32 corresponds to a sequence (2)' (indicated in the diagram by a circled number), which is a sequence wherein the entire base sequence of the RGM249 gene (gene 2) is shifted one base towards the 5' end.

Similarly with the case for FIG. 7, in FIG. 8 also, the design of chemically modified siRNA is carried out using Stealth RNAi Designer. That is, FIG. 8(b) lists, among the results of function prediction using Stealth RNAi Designer, those that have a high predicted value for functioning as an siRNA. The details of chemical modification by Stealth RNAi have not been made publicly available, since they are an industrial secret, but they are obtainable upon ordering from Invitrogen Corporation.

It is expected that any double stranded siRNA whereof the sense strand is a sequence listed in FIG. 8(b), suppresses the expression of the RNA of the RGM249 gene (gene 2), similarly to the siRNA of FIG. 8(a), (1) and (2).

Further, the double stranded siRNA can be Stealth RNAi, but it is not particularly restricted, and can have overhangs with a length of two bases on the 3' end of both the sense strand and the antisense strand. Additionally, these RNA can be not only double stranded siRNA, but also single stranded shRNA wherein a hairpin loop sequence with a length of 4 bases or more is disposed in between a sense sequence (corresponding to the sense strand) and an antisense sequence (corresponding to the antisense strand). Further, there is no particular limit on the length of this hairpin loop sequence, but it can be, for example, 8 bases long. This is because it is expected that any of these will suppress the expression of the RNA of the RGM249 gene (gene 2).

FIG. 8(c) is a diagram showing the location on the entire length of the sequence of the RGM249 gene (gene 2) that corresponds to the sequence of the sense strand of FIG. 8(a) (1) and (2). The underlined portions indicated by the reference numbers (1) and (2) correspond to the sequences of the sense strands of (1) and (2).

FIG. 9 is a diagram for explaining the method of transfecting the RNA into cells. For example, in order to perform the experiments described in the following embodiments using siRNA and the like including the specific double stranded RNA designed based upon (1) the double stranded RNA of the RGM249 gene (gene 2), (2) the double stranded RNA of the RPL22 gene, or the above-described RGM249 gene (gene 2), these RNA must first be transfected into mammalian cells. At this time, as a transfection reagent, for example, Lipofectamine 2000 (registered trademark), manufactured by Invitrogen Corporation, may be used.

Next, after having cultured under predetermined conditions these mammalian cells wherein these RNA have been transfected, these RNA are extracted from these mammalian cells. Whereafter, by performing RT-PCR using these extracted RNA, the changes in the expression of each of the types of RNA due to transfection with these RNA can be detected.

FIG. 10 is a schematic diagram showing the effect of RNAi. The siRNA becomes one portion of an RNA-nuclease complex (RNA-induced silencing complex, or RISC) that targets the complementary cellular mRNA. At this time, the sense strand separates from the antisense strand and is broken down.

Then, the RNA-nuclease complex that includes the antisense strand of siRNA suppresses the expression of the target mRNA within the cell by recognizing and cleaving target mRNA that is complementary to the antisense strand.

Further, the RNA used in RNAi is not restricted to siRNA having overhangs with a length of two bases on the 3' end of both the sense strand and the antisense strand, but can also be single stranded shRNA wherein a hairpin loop sequence with a length of 4 bases or more is disposed in between a sense sequence (corresponding to the sense strand) and an antisense sequence (corresponding to the antisense strand). Further, there is no particular upper limit on the length of this hairpin loop sequence, but it can be, for example, 8 bases long. This is because for such shRNA, the hairpin loop sequence thereof is cleaved, and changes to siRNA.

Herebelow, the uses of the two RNA genes of the present mode of embodiment shall be explained. Since the two RNA genes of the present mode of embodiment both have functions of regulating the expression of the telomerase reverse transcriptase gene (hTERT), they can regulate the expression of the telomerase reverse transcriptase gene (hTERT) within mammalian cells.

More specifically, the two RNA genes of the present mode of embodiment are the key to understanding the molecular mechanism of carcinogenesis, and will prove useful for the development of an anti-cancer treatment using telomerase suppression (molecular targeting treatment). Whereas telomerase, being a large molecule of 4.0 kb, is especially difficult for humans to control, said genes are molecules of 400 bp or less, so it can be thought that regulation of genetic expression would be easier. In recent years, much anti-cancer research has been carried out, and although the development of fields concerning the administration thereof has been advancing, the discovery of original samples that are to be administered has been slow. Since reports about factors that are related extremely directly to cancer have been few, the investigation of this region, and the fact that this molecule is related to the theme of cancer eradication, can be thought to be innovative and groundbreaking.

Specifically, regarding the RGM376 gene (gene 1), if the RNA that is a transcription product thereof is overexpressed, the expression of the telomerase reverse transcriptase gene (hTERT) is suppressed. Thus, by making the RNA that is a transcription product of the RGM376 gene (gene 1) be overexpressed, telomerase activation can be suppressed, and as a result, carcinogenesis can be suppressed. Additionally, regarding the RGM376 gene (gene 1), it can be used as a research tool for investigating the molecular mechanism of carcinogenesis.

Additionally, the expression vector constructed by linking the RGM376 gene (gene 1) to a vector, when transfected into a cell, suppresses the expression of the telomerase reverse transcriptase gene (hTERT). Whereby, this expression vector suppresses the activation of telomerase, and as a result, can suppress carcinogenesis.

Therefore, when a medication containing RNA that is a transcription product of the RGM376 gene (gene 1) or the abovementioned expression vector is administered to the human body, the expression of the telomerase reverse transcriptase (hTERT) gene is suppressed. Thus, this medication suppresses the activation of telomerase, and as a result, is suited for being used as a cancer treating agent that can suppress carcinogenesis.

Additionally, the various types of RNA that are designed based upon the RGM376 gene (gene 1), such as siRNA and shRNA, suppress the expression of the telomerase reverse transcriptase (hTERT) gene by suppressing the expression of the RGM376 gene (gene 1). Additionally, RNA (RNA cocktail or RNA pool) containing a plurality of types of double stranded RNA made by cleaving with Dicer or the like double stranded RNA including RNA that is a transcription product of RGM376 (gene 1) and RNA that includes a base sequence that is complementary to this RNA, also suppress the expression of the telomerase reverse transcriptase (hTERT) gene, by similarly suppressing the expression of the RGM376 gene (gene 1). Whereby, these various types of RNA suppress telomerase activity, and as a result, can suppress carcinogenesis.

Additionally, a complex comprised by linking various types of RNA such as these siRNA and shRNA with a substance that promotes (induces) uptake into lipids and cells such as cholesterol, as described in Non-Patent Citation 2, suppresses the expression of target mRNA (RGM376 gene (gene 1)) continuously and for a long time within mammalian cells such as in the human body. Whereby, the various types of complexes such as this RNA-cholesterol complex, by suppressing the expression of the RGM376 gene (gene 1) over a long time, suppress the expression of the telomerase reverse transcriptase (hTERT) gene. Additionally, if the complex is a complex that can be obtained by linking an uptake promoter (inducer) to the various types of RNA, the uptake efficiency into cells will also improve. Therefore, these various types of RNA suppress telomerase activity over a long time, and as a result, can suppress carcinogenesis over a long period of time.

For this reason, medications containing various types of RNA such as the abovementioned siRNA and shRNA, as well as the abovementioned RNA-cholesterol complexes, suppress the expression of the telomerase reverse transcriptase gene when administered to the human body. Whereby, these medication suppress telomerase activity, and as a result, can suitably be used as cancer treatment agents that can suppress carcinogenesis. In particular, medications containing the abovementioned RNA-cholesterol complex have the advantage that the intervals between administration to the human body can be made long, because they suppress carcinogenesis over a long period of time, due to the abovementioned mechanism.

On the other hand, additionally, regarding the RGM249 gene (gene 2), since the expression of RNA that is the transcription product, and the expression of hTERT (canceration of the cell) synchronize, it can be used as a research tool for investigating the molecular mechanism of carcinogenesis. Additionally, an expression vector that is constructed by linking the RGM249 gene (gene 2) to a vector so as to enable expression, promotes the expression of the telomerase reverse transcription (hTERT) gene when transfected into a cell, and promotes telomerase activity and causes canceration to occur. Therefore, this expression vector can also be used as a research tool.

Additionally, the various types of RNA such as siRNA and shRNA that are designed based upon the RGM 249 gene (gene 2), suppress the expression of the telomerase reverse transcriptase (hTERT) gene by suppressing the expression of the RGM249 gene (gene 2). Additionally, RNA (RNA cocktail or RNA pool) containing a plurality of types of double stranded RNA made by cleaving with Dicer or the like double stranded RNA including RNA that is a transcription product of RGM249 (gene 2) and RNA that includes a base sequence that is complementary to this RNA, also suppresses the expression of the telomerase reverse transcriptase (hTERT) gene, by similarly suppressing the expression of the RGM249 gene (gene 2). Therefore, these various types of RNA suppress telomerase activity, and as a result, can suppress carcinogenesis.

Additionally, a complex comprised by linking various types of RNA such as these siRNA and shRNA with a substance that promotes (induces) uptake into lipids and cells such as cholesterol, as described in Non-Patent Citation 2, suppresses the expression of target mRNA (RGM249 gene (gene 2)) continuously and for a long time within mammalian cells such as in the human body. Whereby, the various types of complexes such as this RNA-cholesterol complex, by suppressing the expression of the RGM249 gene (gene 2) over a long time, suppress the expression of the telomerase reverse transcriptase (hTERT) gene. Additionally, if the complex is a complex that can be obtained by linking an uptake promoter (inducer) to the various types of RNA, the uptake efficiency into cells will also improve. Therefore, these various types of RNA suppress telomerase activity over a long time, and as a result, can suppress carcinogenesis over a long period of time.

Because of this, medicines containing the abovementioned various types of RNA such as siRNA and shRNA, or the abovementioned RNA-cholesterol complexes, suppress the expression of the telomerase reverse transcriptase (hTERT) gene when administered to the human body. Whereby, these medicines suppress telomerase activity, and as a result, can optimally be used as cancer treatment agents that can suppress carcinogenesis. Particularly, medicines containing the abovementioned RNA-cholesterol complexes have the advantage of making the interval of administration to the human body longer, because they suppress carcinogenesis over a long period, due to the abovementioned action mechanism.

The modes of embodiment of the present invention have been stated with reference to drawings, but these are examples of the present invention, and various constitutions other than the abovementioned ones can be utilized.

For example, in the abovementioned mode of embodiment, an siRNA is used that has, as a sense chain, a sequence that is a portion of the base sequence of the RGM376 gene (gene 1) or the RGM249 gene (gene 2), and is predicted by BLOCK-iT RNAi Designer, but other RNAi design software may also be used, or RNA may be generated randomly and an siRNA that causes RNAi activity can be selected by experiment. An siRNA that suppresses the expression of the RGM376 gene (gene 1) or the RGM249 gene (gene 2) can also be obtained in this way.

Herebelow, the present invention shall be further explained using embodiments, but the present invention is not restricted to these.

<Investigation of miRNA Generation>

Figure 11:
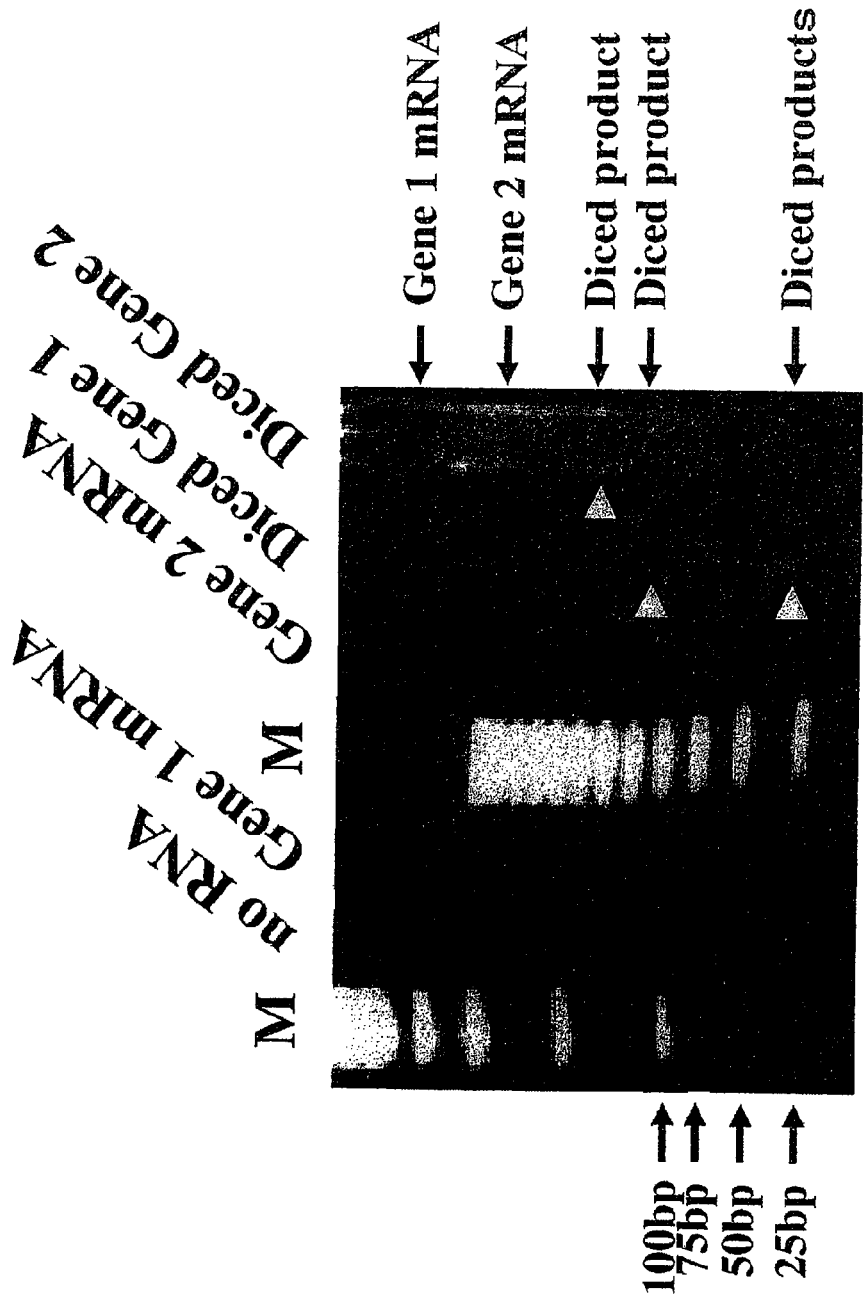
[FIG. 11] Electrophoresis diagram for explaining dicing of two types of mRNA by Dicer.

FIG. 11 is an electrophoresis diagram for explaining the cleaving of two types of mRNA with Dicer. Prior to conducting the below-described embodiments, we conducted an investigation of the generation of miRNA from the RGM376 gene (gene 1) and the RGM249 gene (gene 2).

Here, the method of experiment was conducted as below. That is, the RGM249 and RGM376 genes were implanted into expression vectors having T7 promoters inside, and using a mass RNA regulation method using T7 RNA polymerase (T7 RiboMAX (registered trademark) Express Large Scale RNA Production System: Promega), RNA of both RGM249 (gene 1 mRNA) and RGM376 (gene 2 mRNA) were generated, and were cleaved with an Rnase III family Dicer (Turbo Dicer: Genlantis). As a result, RNA corresponding to Diced gene 1 and Diced gene 2 were obtained. Thereafter, the reaction products were electrophoresed with a 30% acrylamide gel and visualized.

When mRNA of the RGM376 gene (gene 1) and the RGM249 gene (gene 2) were cleaved with Dicer, bands each having a size of approximately 25 bp were generated. The existence of these bands with a size of approximately 25 bp suggested that by cleaving the RGM376 gene (gene 1) and the RGM249 gene (gene 2) inside cells, miRNA was being generated.

Embodiment 1

In the present embodiment, a functional analysis was carried out of a gene (RGM376 gene (gene 1)) that suppresses the expression of the mRNA of the telomerase reverse transcriptase gene hTERT.

More specifically, in the present embodiment, (1) as an investigation of gene expression, comparison of a liver cancer cell line and a primary-cultured hepatocyte cell line, and comparison of tissue from a cancerous portion and a noncancerous portion of liver was conducted, and (2) as a transfection of a gene by a forced expression vector, an analysis of a growth curve and telomerase activity was conducted.

Further, when conducting the abovementioned experiments, in order to ensure that a mutation is not occurring during the process of PCR, the sequence of PCR products was confirmed.

Figure 12:
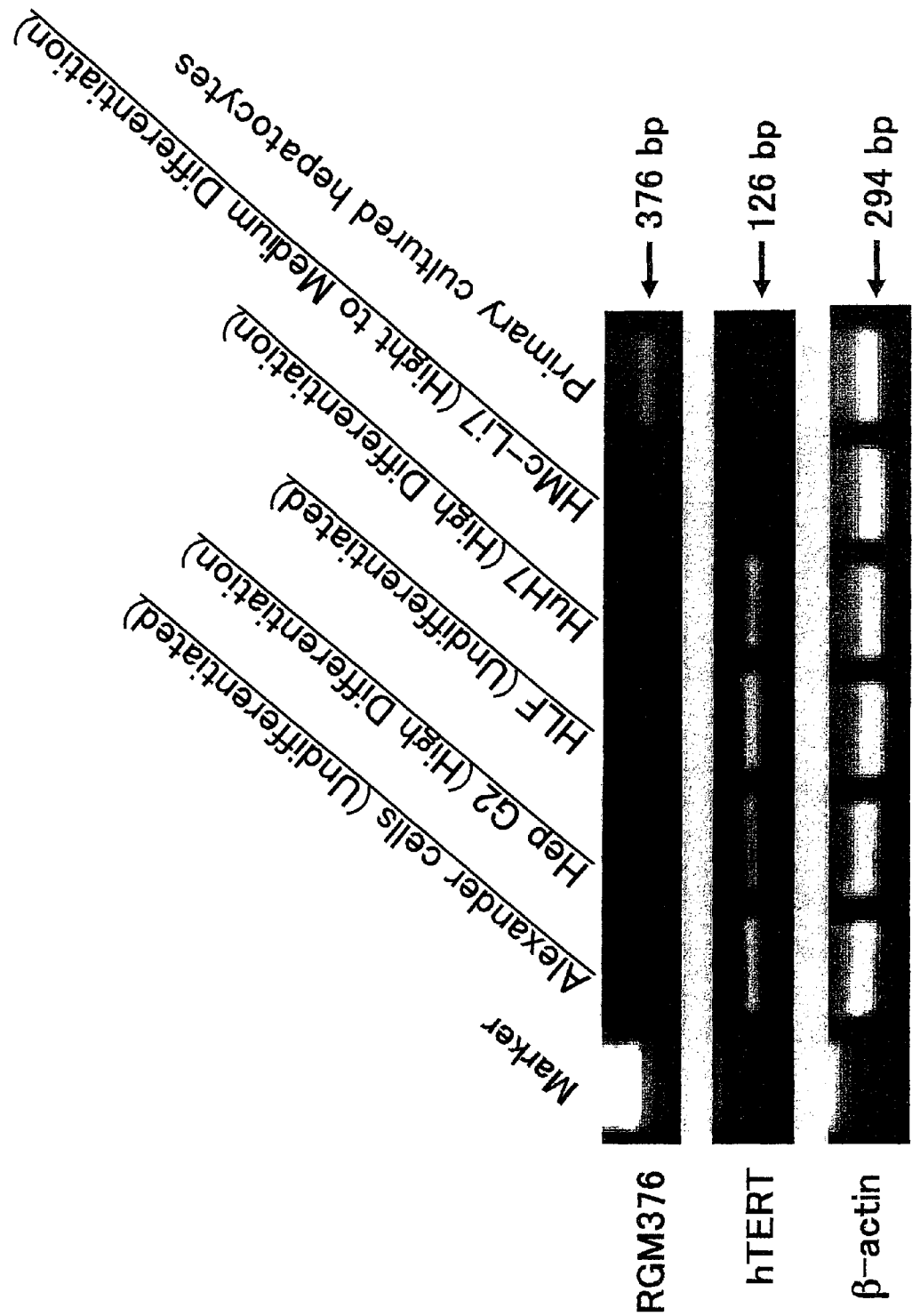
[FIG. 12] Electrophoresis diagram showing differentiation specific expression of RGM376 in liver cancer cells.

FIG. 12 is an electrophoresis diagram showing the differentiation specific expression of RGM376 in liver cancer cells. Using Alexander cells (undifferentiated), HepG2 (high differentiation), HLF (undifferentiated), HuH7 (high differentiation), HMc-Li7 (high to medium differentiation), and primary cultured hepatocytes, and RT-PCR and electrophoresis, the level of expression of the mRNA of the RGM376 gene, the hTERT gene, and the β-actin gene inside cells was examined.

Here, the experiment was done in the following manner. That is, the expression of the RGM249, the hTERT, and the β-actin gene in 5 types of liver cancer cell lines was detected by using the RT-PCR method, reacting for 30-35 cycles, and conducting electrophoresis. Primary cultured hepatocytes (KIA) were reacted under the same conditions as the liver cancer cell lines, and the expression of each gene was detected. As the detection method, electrophoresis was done with a 1% agarose gel.

The results of the electrophoresis were that the expression of the hTERT gene increased, and the expression of the RGM376 gene decreased. On the other hand, in normal cells, the expression of the hTERT gene decreased, and the expression of the RGM376 gene increased. That is, in liver cancer cell lines, differentiation specific expression was recognized. If the differentiation specific expression results in tissue from cancerous portions and noncancerous portions of liver obtained in FIG. 12, and the unshown clinical results are summarized, they are as follows.

(1) Among tissue from noncancerous portions, the expression of the RGM376 gene was recognized in 84.4% (38 of 45 samples, unshown portions included).

(2) In comparisons with clinical parameters (not shown), the expression of the RGM376 gene in cancerous portions was significant according to t-tests for tumor size (P=0.003), tumor number (P=0.047), level of differentiation (P=0.021), and vascular infiltration (P<0.001).

(3) In comparisons in terms of recurrence prediction factors (not shown), a strong correlation with capsule infiltration (P=0.001) was seen.

If all of these results are considered in toto, it can be presumed that when the strength of expression of the RGM376 gene is low, the level of differentiation of cancer cells becomes high, and capsule infiltration becomes low. On the other hand, if the strength of expression of the RGM376 gene is high, the level of differentiation of cancer cells becomes approximately medium, and the capsule infiltration becomes high.

Figure 13:
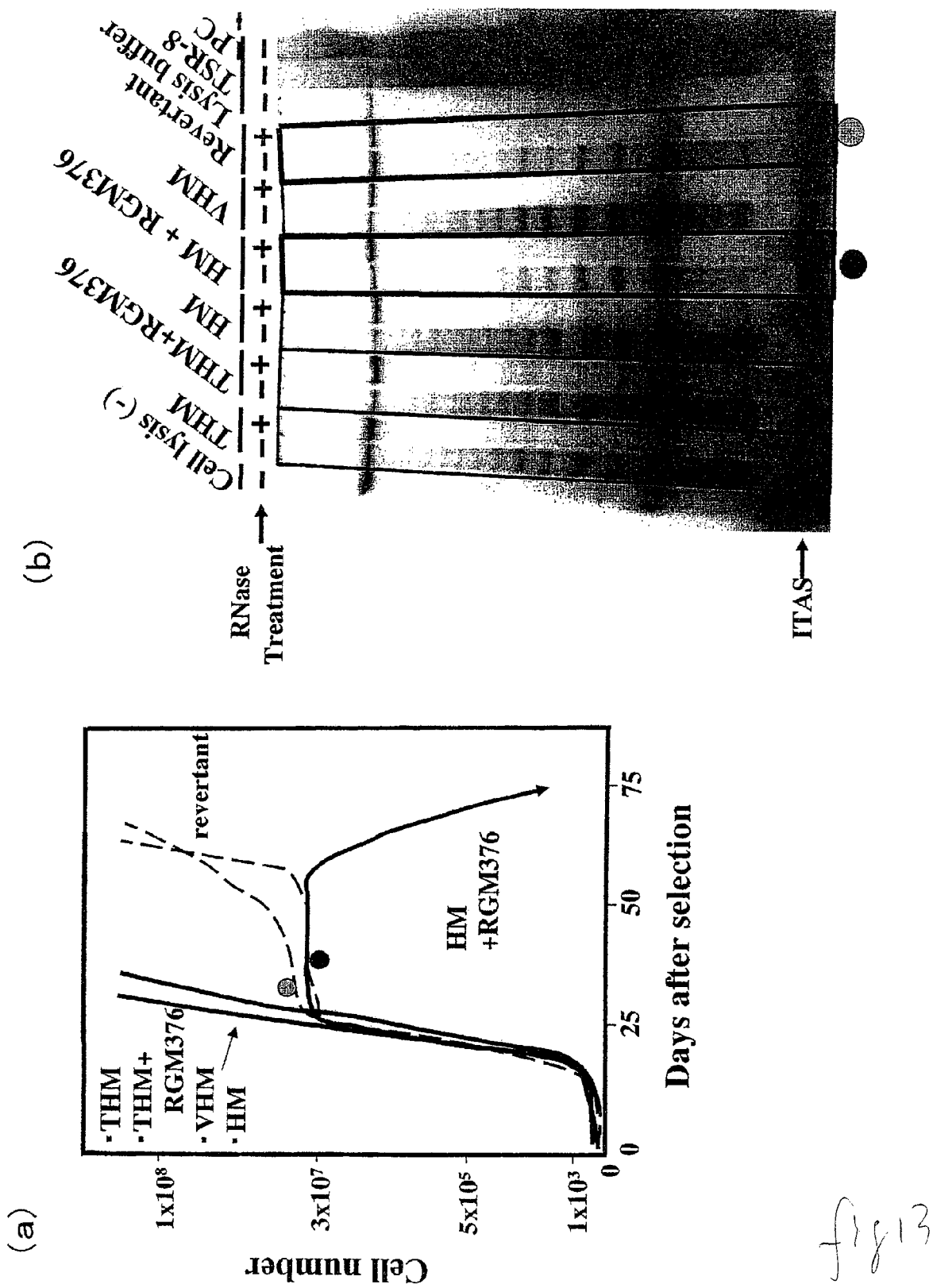
[FIG. 13] Electrophoresis diagram and graph for explaining suppression of telomerase activity due to overexpression of RGM376.

FIG. 13 is a graph and an electrophoresis diagram for explaining the suppression of telomerase activity due to the overexpression of RGM376. In FIG. 13(a), the horizontal axis shows the number of days of culturing after selection, and the vertical axis shows the number of cells. Further, HM indicates the HMc-Li7 line (bought from Clontech), THM indicates HM telomerized by pLXIN-hTERT, and VHM indicates HM with only pLXIN (obtained through the courtesy of Dr. Tahara of Hiroshima University Department of Medicine) transfected. HM+RGM376 indicates gene transfected cell lines wherein RGM376 is transfected into HMc-Li7 cell lines.

Here, the method of experiment was carried out as follows. That is, regarding liver cancer cell line HM, cell lines where RGM376 was transfected into HM cell lines, THM cell lines (provided by Hisatoshi Tahara of Hiroshima University) wherein hTERT is forcibly expressed in HM cell lines, and VHM cell lines wherein only the vector is transfected, were used. Further, RGM376 was transfected by implanting into the expression vector pEGFP-C1 (Clontech at the time). Additionally, the telomerase activity in cells wherein RGM376 and the like are transfected was detected using the TRAPeze detection kit (Oncor Inc.). During this detection, the detection was done by using a reagent provided by Oncor and following the indicated protocol.

As shown in the graph of FIG. 13(a), when the RGM376 gene is overexpressed in HMc-Li7 cell lines, cells that were originally in a growth phase entered a growth suppression phase after approximately 25 days, and the number of cells started decreasing after approximately 50 days. On the other hand, when the RGM376 gene is not overexpressed in HMc-Li7 cell lines, the growth phase continues undisturbed. Additionally, if the RGM376 gene and the hTERT gene are overexpressed together in HMc-Li7 cell lines, the growth phase continues undisturbed. On the other hand, in revertant cell lines (Revertant), the growth suppression phase was entered approximately 25 days later, and the number of cells started increasing after approximately 50 days.

FIG. 13(b) shows the results of having done RT-PCR and electrophoresis in each of the THM, THM+RGM376, HM, HM+RGM376, VHM, and Revertant cell lines, for both the cases where Rnase treatment was carried out and not carried out. Further, for the HM+RGM376 and Revertant cell lines, samples were taken on the day marked with a black circle in FIG. 13(a).

Figure 14:
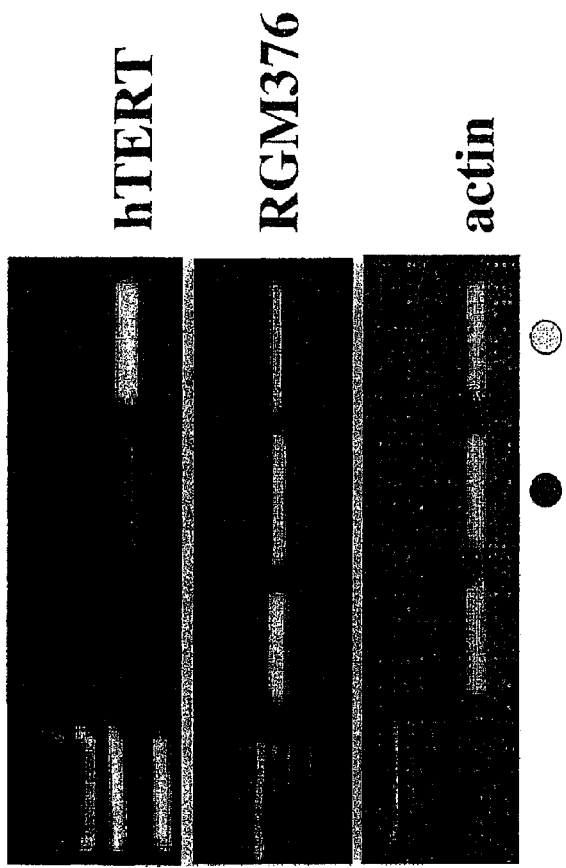
[FIG. 14] Electrophoresis diagram showing expression of hTERT and RGM376 in a transformed cell.

FIG. 14 shows an electrophoresis diagram of the expression of hTERT and RGM376 in transformed cells. For cells in a growth period (in growth), a suppression period (in suppression), and revertants (in revertant), the amount of expression of mRNA of the hTERT gene, the RGM376 gene, and the β-actin gene were examined.

At this time, the method of experimentation was as follows. That is, in cells genetically transfected with RGM376 in FIG. 13, the expression of each gene was examined by RT-PCR in the growth phase, suppression phase, and revertant phase due to the beginning of the dropping out of the transfected gene, using RNA treated by Dnase. For the RNA purification, the SV total RNA isolation system of Promega was used.

As a result, in the growth phase, the amount of expression of the hTERT gene was low, while the amount of expression of the RGM376 gene was high. Additionally, during the suppression phase, the amount of expression of the hTERT gene was low, while the amount of expression of the RGM376 gene was high. However, in the suppression phase, in comparison with the growth phase, the amount of expression of the hTERT gene was high, while the amount of expression of the RGM376 gene was low. On the other hand, in revertant cell lines, the amount of expression of the hTERT gene was high, while the amount of expression of the RGM376 gene was low.

From these results, regarding gene expression, it can be seen that in highly differentiated cancer in comparison with undifferentiated cancer, the RGM376 is highly expressed. Additionally, it can be seen that the amount of expression of the RGM376 gene is strongly correlated to clinical parameters that relate to the degree of malignancy of cancer (tumor size, tumor number, differentiation, vascular infiltration). Whereby, it is suggested that the expression of the RGM376 gene is related to the degree of differentiation of tumors. That is, it is suggested that the RGM376 gene has a function of suppressing telomerase activity within cells, and suppressing the canceration of cells.

Additionally, it is suggested that the overexpression of the RGM376 gene has a function of suppressing the growth of cells that have passed the quiescent phase, and aging cells, and promoting cell death. Additionally, it is suggested that the overexpression of the RGM376 gene has a function of decreasing telomerase activity. Further, it is suggested that the overexpression of the RGM376 gene has a function of decreasing the amount of expression of mRNA of the hTERT gene. That is, it can be presumed that the RGM376 gene is a gene that has a telomerase-mediated (hTERT) cancer suppressing activity.

Figure 15:
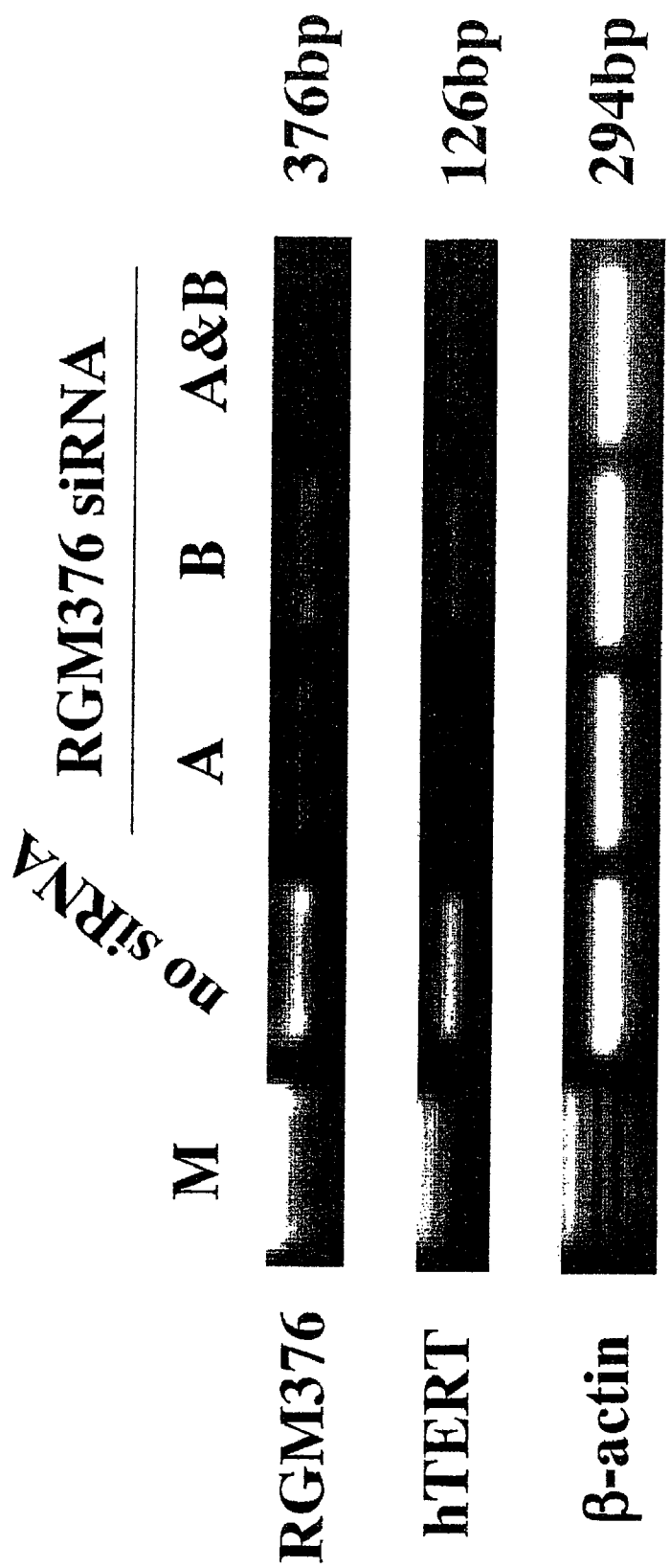
[FIG. 15] Electrophoresis diagram showing expression of a gene in an RGM376 siRNA-transfected cell.

FIG. 15 is an electrophoresis diagram showing the expression of genes in RGM376 siRNA transfected cells. Cells not transfected with siRNA were controls, and as an siRNA against the RGM376 gene, the siRNA comprising the abovementioned A and B sequences was used. RT-PCR and electrophoresis was done on cells wherein each of these siRNA was transfected, for the RGM376 gene, the hTERT gene and the β-actin gene. Additionally, the case where A and B were mixed and transfected was also examined.

At this time, the method of experimentation was as follows. That is, the RGM376 siRNA was designed using the Block-it RNAi designer (homepage) of Invitrogen Corporation, and the two types of siRNA synthesized by said company, A and B, were genetically transfected using Lipofectamine 2000, into the liver cancer cell line HLF at a transfection concentration of 25 nM. Further, a mixture of 25 nM each of A and B was also transfected. Further, regarding the expression of each gene, after RNA was purified from the transfected cells by the same method as FIG. 14, detection was done by the RT-PCR method.

Figure 16:
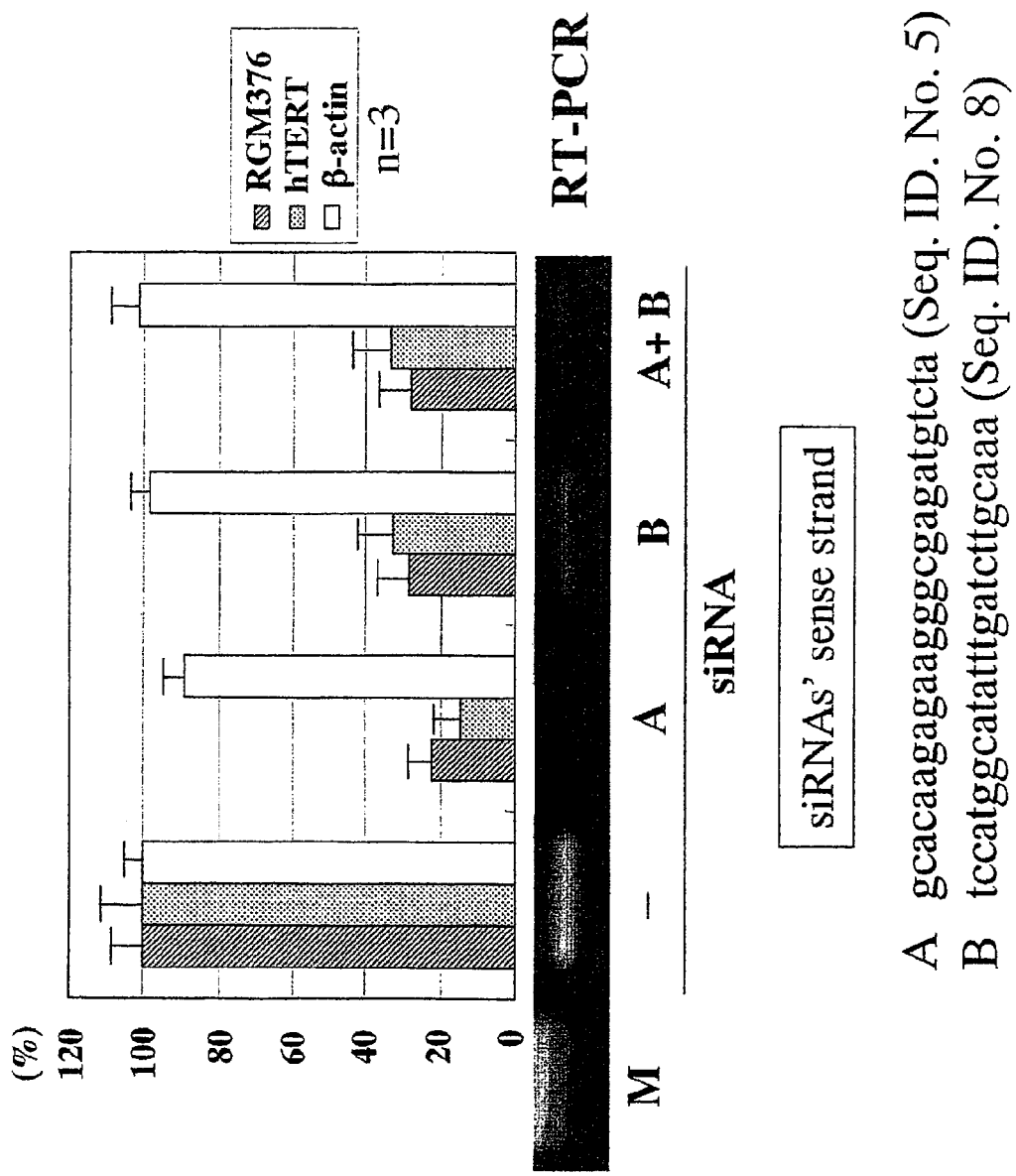
[FIG. 16] Electrophoresis diagram and graph summarizing hTERT results of suppression due to RGM376 siRNA.

FIG. 16 is an electrophoresis diagram and graph summarizing the hTERT suppression results due to RGM376 siRNA. Additionally, FIG. 16 also shows the sequence of the sense chain of the siRNA (A and B) used in this experiment.

At this time, the method of experimentation was as follows. That is, the transfection of siRNA shown in FIG. 15 was attempted 3 times, the degree of suppression of expression of RGM376 was examined by RT-PCR, and at the same time, the strength of expression was measured using a densitometer on an electrophoresis image, and this is shown in a bar graph standardized by the measured values for no siRNA.

As shown in FIG. 16, if the expression of the RGM376 gene is suppressed by RGM376 siRNA, the expression of the hTERT gene is also similarly suppressed. Among the RGM376 siRNA, the suppression effect is best when A alone is used. Additionally, among the RGM376 siRNA, even when B alone is used, an excellent suppression effect was obtained, but the suppression effect was lower than for A. Further, among the RGM376 siRNA, when both A and B were transfected, an excellent suppression effect was obtained, but the suppression effect was lower than for A.

Accordingly, if the expression of the RGM376 gene is suppressed by RGM376 siRNA, the expression of the hTERT gene is also similarly suppressed. Whereby, telomerase activity can be suppressed by RGM376 siRNA, and as a result, the canceration of cells can be suppressed.

Embodiment 2

In the present embodiment, a functional analysis was carried out of a gene (RGM249 gene (gene 2)) that is expressed synchronously with telomerase reverse transcriptase gene hTERT mRNA.

In more detail, (1) expression in liver cancer cell lines was examined with RT-PCR, (2) expression in liver tissue was examined with RT-PCR, (3) the relation to genes that relate to telomerase formation was examined, and (4) dsRNA derived from genes whose involvement is suggested was expressed, and transfection with siRNA was done, and observations with RT-PCR, Cell proliferation assay, MTT assay, and morphological changes were carried out.

Further, when performing the abovementioned experiments, in order to ensure that no mutations have occurred in the process of PCT, the sequence of PCR products were confirmed.

Figure 17:
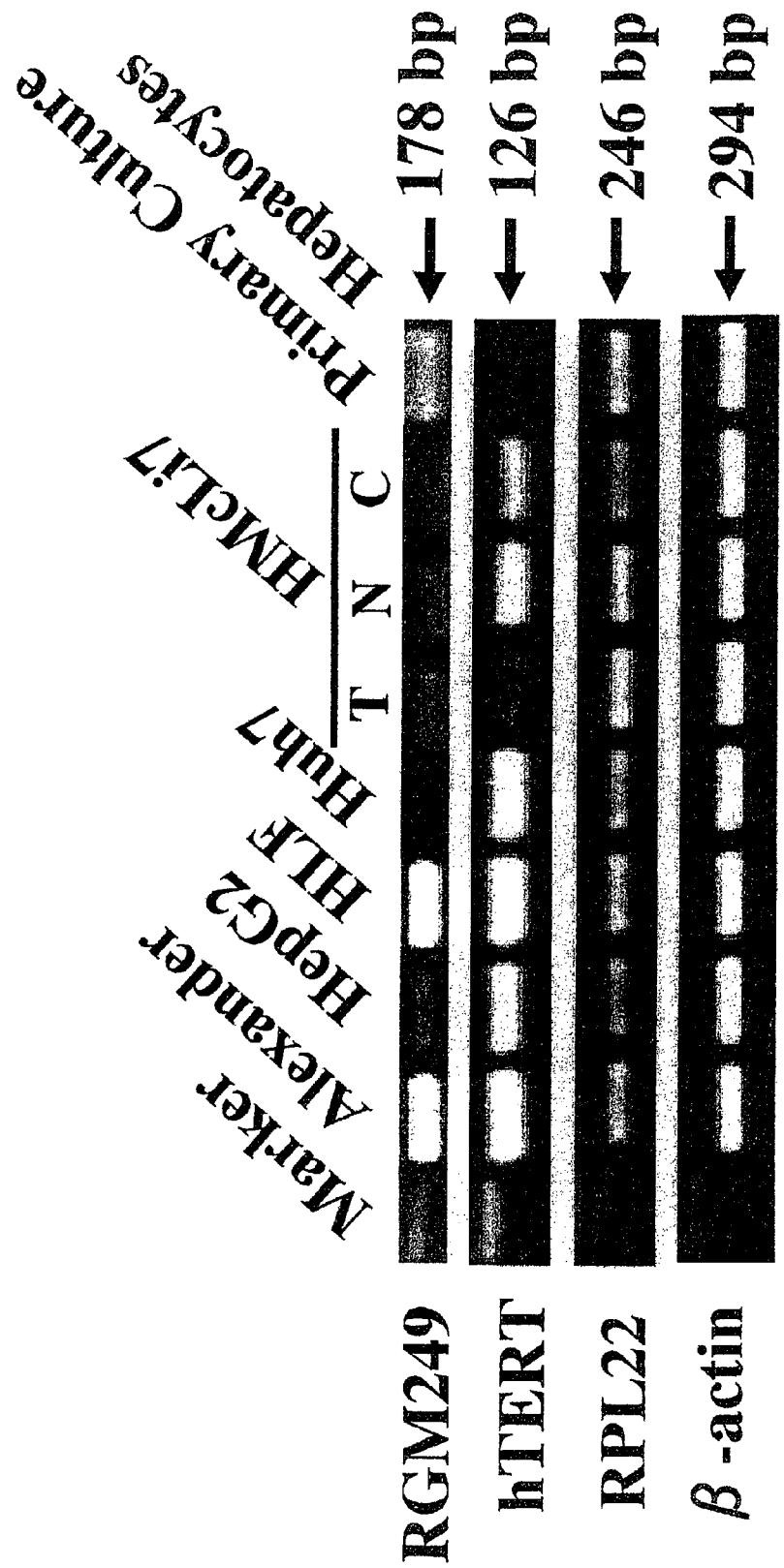
[FIG. 17] Electrophoresis diagram showing differentiation specific expression of RGM249 in a liver cancer cell.

FIG. 17 is an electrophoresis diagram showing differentiation specific expression of RGM249 in liver cancer cells. Using Alexander cells (undifferentiated), HepG2 (high differentiation), HLF (undifferentiated), HuH7 (high differentiation), HMc-Li7 (T, N, C), and primary cultured hepatocytes as samples, the level of expression of the mRNA of the RGM376 gene, the hTERT gene, and the β-actin gene inside cells was examined by RT-PCR and electrophoresis.

Here, the experiment was done in the following manner. That is, by the same method as in FIG. 12, the expression of RGM249, hTERT, RPL22, and β-actin was examined by the RT-PCR method. Further, in FIG. 17, for HMc-Li7, T indicates total RNA, N indicates RNA extracted from nucleus, and C indicates RNA inside cells.

As a result of electrophoresis, for the RGM249 gene, expression in liver cancer cell lines and primary cultured hepatocyte cell lines expressing the hTERT gene was seen. Additionally, in cancer cells, the expression of the hTERT gene increased, and the expression of the RGM249 gene synchronously increased. On the other hand, in normal cells, the expression of hTERT cells decreased. That is, differentiation-specific expression was seen in liver cancer cell lines.

Figure 18:
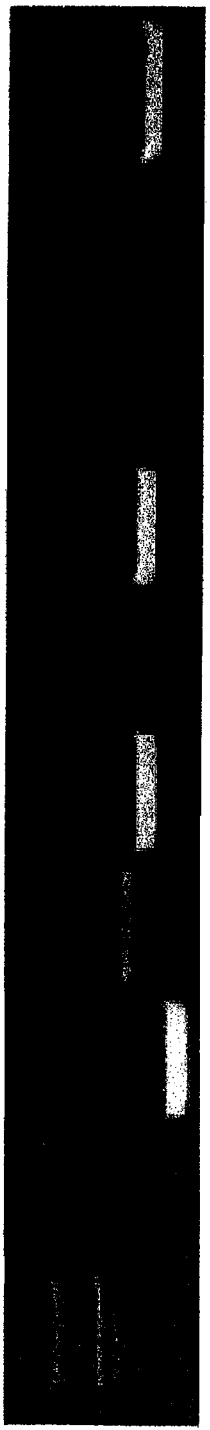
[FIG. 18] Electrophoresis diagram showing expression of genes due to transfection of RGM249 dsRNA into HMc-Li7.

FIG. 18 is an electrophoresis diagram showing the expression of genes due to the transfection of RGM249 dsRNA into HMc-Li7. dsRNA designed to suppress the expression of RGM249 was transfected into HMc-Li7 cells, and RT-PCR and electrophoresis was performed on each of the hTERT, hTR, TEP1, dyskerin, RPL22, Nola3, and RGM249 genes.

Here, the method of experimentation was as follows. That is, RGM249 dsRNA was implanted into the restriction enzyme portion of a vector, Litmas 28i (New England BioLab), having a T7 promoter in dual directions, and a double stranded RNA was generated with T7 RNA polymerase. After this double stranded RNA was purified, using transformed cells wherein Lipofectamine Plus is transfected into HM, the strength of expression of the telomerase related genes (hTERT, hTR, TEP1, Dyskerin, RPL22, Nola3, RGM249) was measured by a densitometer, and the results shown in FIG. 18 were obtained.

As a result thereof, in HMc-Li7 cells wherein the expression of the RGM249 gene was suppressed, the expression of the hTERT gene and the RPL22 gene were also synchronously suppressed. Whereby, it is suggested that the RGM249 gene has a function of promoting the expression of the hTERT gene and the RPL22 gene.

Figure 19:
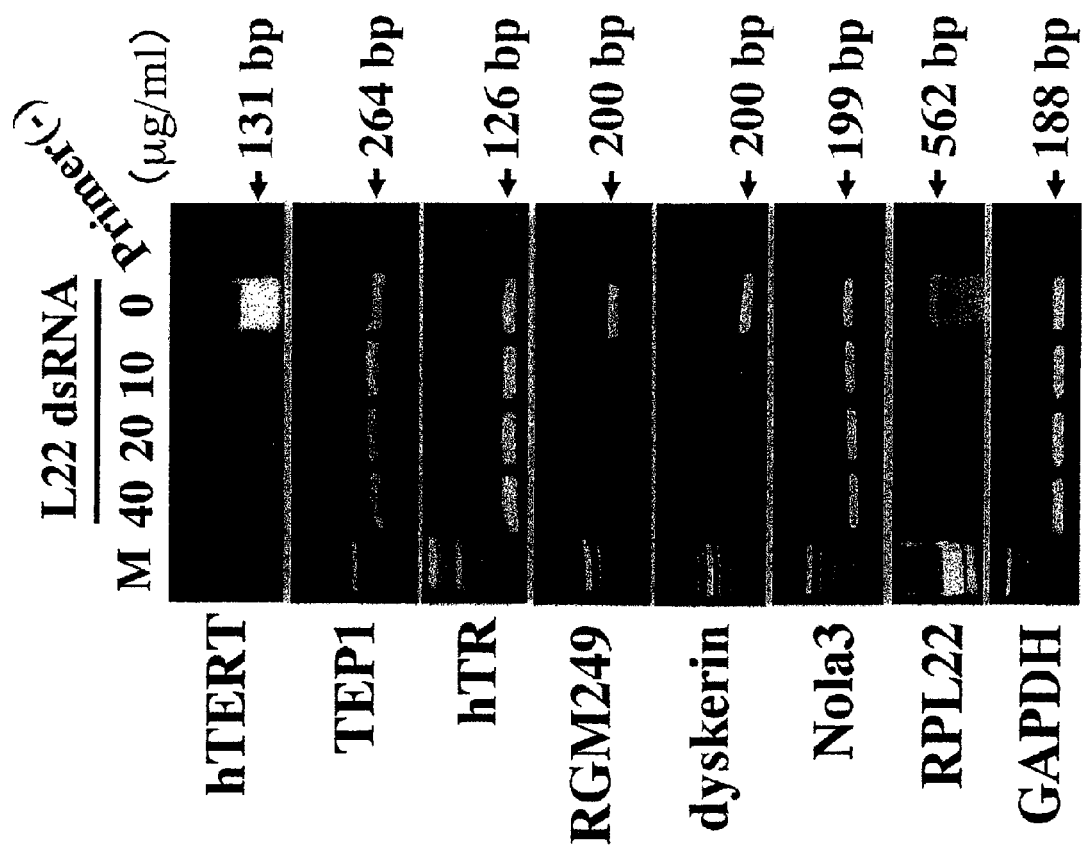
[FIG. 19] Electrophoresis diagram showing expression of genes due to transfection of RPL22 dsRNA into HM.

FIG. 19 is an electrophoresis diagram showing the expression of a gene due to transfection of RPL22 dsRNA into HM. dsRNA designed to suppress the expression of RPL22 was transfected into HMc-Li7 cells, and RT-PCR and electrophoresis was performed for each of the hTERT, TEP1, hTR, RGM249, dyskerin, Nola3, RPL22, and GAPDH genes.

At this time, the experimental method was as follows. That is, RPL22 cDNA (TOYOBO) was purchased, and after culturing in an *E. coli* strain, plasmid DNA was purified, and the RPL22 cDNA was implanted into the restriction enzyme portion of Litamas 28i, and dsRNA of RPL22 was obtained similarly to FIG. 18, and was transfected into HM using Lipofectamine Plus (Invitrogen). The abovementioned dsRNA was transfected into transformed cells obtained in this way, at transfection concentrations of 40, 20, 10, and 0 μg/ml. After this, for each gene, expression was examined using RT-PCR, and electrophoresis was performed.

As a result, in HMc-Li7 cells wherein the expression of the RPL22 gene is suppressed, the expression of (1) the RGM249 gene, (2) the hTERT gene, and (3) dyskerin were also synchronously suppressed. Whereby, it is suggested that the RPL22 gene has a function of promoting the expression of the RGM249 gene, the hTERT gene, and the dyskerin gene.

Figure 20:
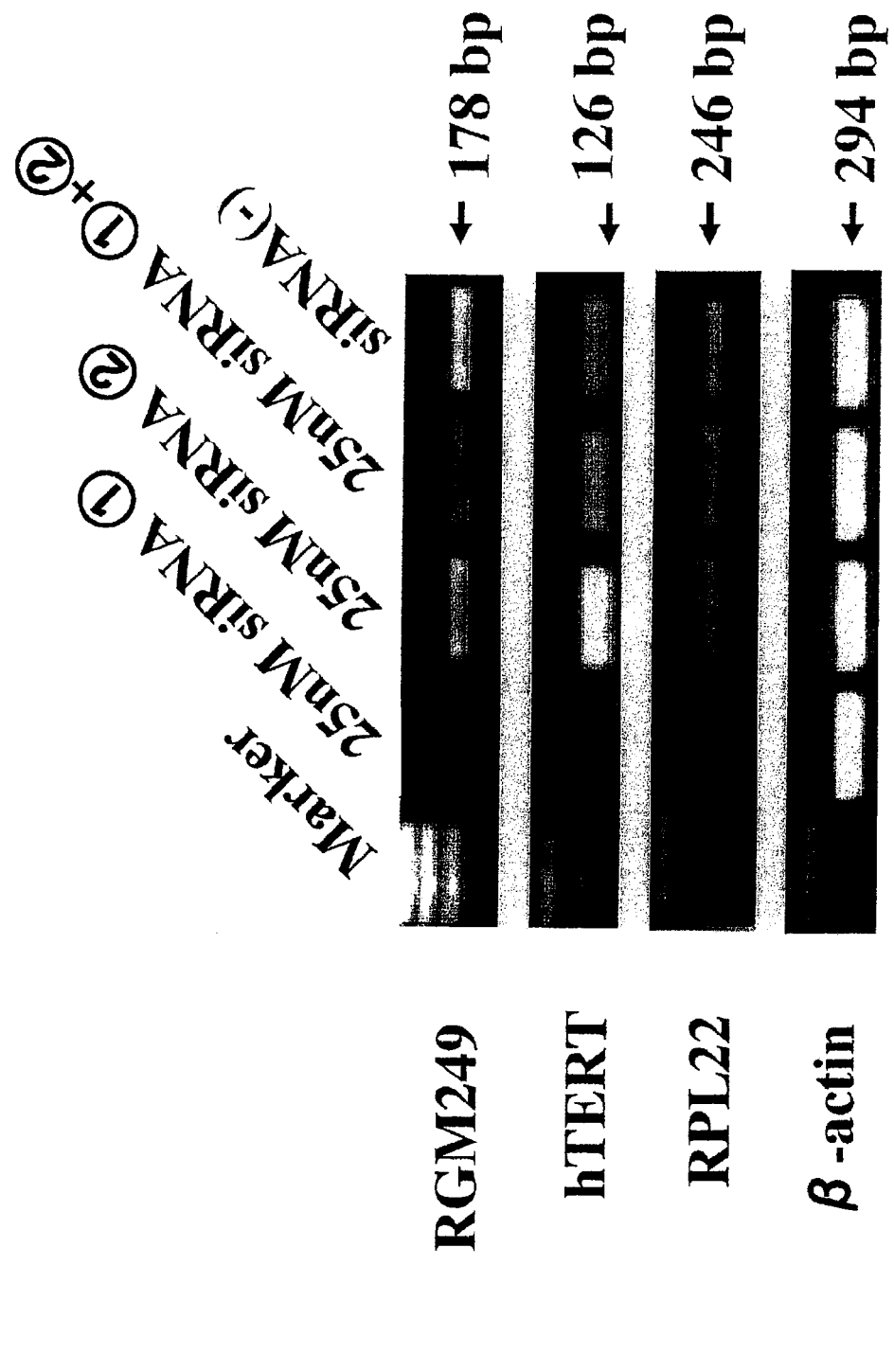
[FIG. 20] Electrophoresis diagram showing expression of genes due to transfection of RGM249-specific siRNA into HLF.

FIG. 20 is an electrophoresis diagram showing the expression of genes due to the transfection of RGM249 specific siRNA into HLF. A specific siRNA designed to suppress the expression of RGM249 (siRNA of the abovementioned (1) (indicated in the figure with a circled number) and (2) (indicated in the figure with a circled number)), and RT-PCR and electrophoresis was done for each of the RGM249, hTERT, RPL22, and the β-actin genes. As a result thereof, in HLF cells wherein the expression of the RGM249 gene was suppressed by siRNA (1), the expression of the hTERT gene and the RPL22 gene were also synchronously suppressed.

At this time, the method of experimentation was as follows. That is, similarly with FIG. 15, the two types of RGM249 siRNA (1) and (2), designed and synthesized by Block-it RNAi designer, was transfected into the liver cancer cell line HLF using Lipofectamine 2000 (Invitrogen), RNA was extracted from the transfected cells, RT-PCR was performed, and the strength of expression was visualized by electrophoresis and detected.

Figure 21:
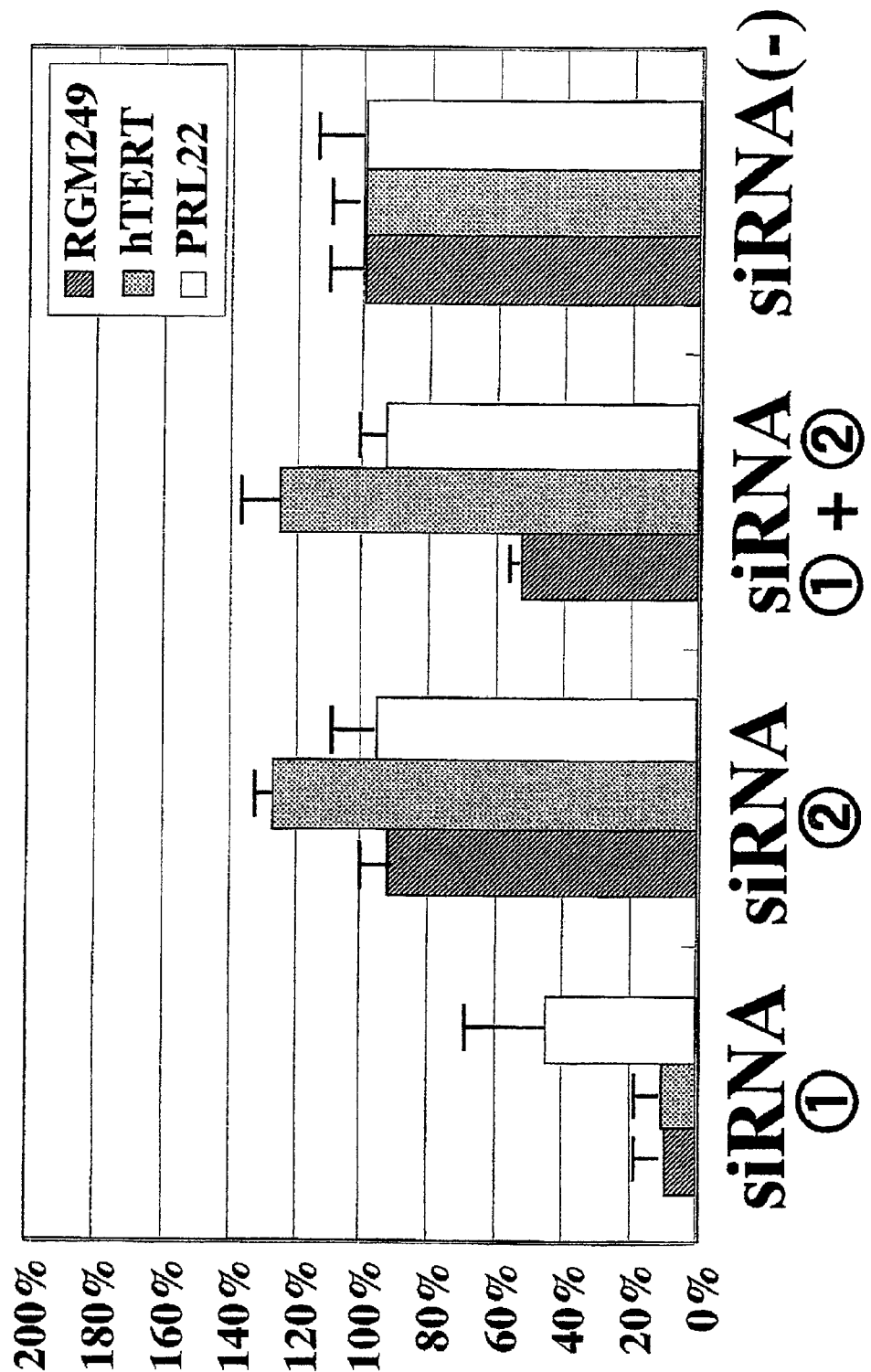
[FIG. 21] Graph summarizing rate of suppression of mRNA expression of each gene after transfection of RGM249-specific siRNA.

FIG. 21 is a graph summarizing the expression suppression rate of the mRNA of each gene after transfection with RGM249 specific siRNA. As shown in FIG. 21, if the expression of the RGM249 gene is suppressed by RGM249 specific siRNA (1) (indicated in the figure with a circled number), the expression of the hTERT gene and the RPL22 gene are also similarly suppressed. Additionally, among the RGM249 specific siRNA, when (2) (indicated in the figure by a circled number) was used alone, and when (1) and (2) were both transfected, the expression suppression effect on the hTERT gene and the RPL22 gene was lower than when (1) was used alone.

Therefore, when the expression of the RGM249 gene is suppressed by RGM249 specific siRNA, the expression of the hTERT gene and the RPL22 gene are also suppressed. Whereby, telomerase activity can be suppressed by RGM249 specific siRNA (1), and as a result thereof, the canceration of cells can be suppressed.

At this time, the method of experimentation was as follows. That is, the transfection experiment examined in FIG. 20 was performed 3 times, the electrophoresis image was image scanned by a densitometer, the measured values were standardized relative to no siRNA, and the degree of suppression of genes due to siRNA was shown with a bar graph.

From these experimental results regarding the RGM249 gene, it was found that the RGM249 gene was expressed in approximately 80% of liver cancer cell lines and liver cancer tissue. Additionally, due to RGM249 specific siRNA genetic transfection experiments, it was found that siRNA derived from RGM249 suppress the expression of the hTERT gene and the RPL22 gene. Further, although not shown in a diagram, when liver tissue was examined, it was found that among the correlations between the various clinical parameters, there was a significant correlation between PIVKA-2, which is a tumor marker for liver cancer, and the amount of expression of the RGM249 gene, by t-test, multivariable analysis, and Pearson's correlation test.

Whereby, it is presumed that in liver cancer cells expressing the hTERT gene, primary cultured liver cells, liver cancer tissue, and non-liver cancer tissue, the RGM249 gene is uniformly expressed. Additionally, there is a possibility that the RGM249 gene is involved in the expression of the hTERT gene and the RPL22 gene. Further, the involvement of the RGM249 gene in carcinogenesis is suggested.

<Relation Between RGM376 and RGM249>

Figure 22:
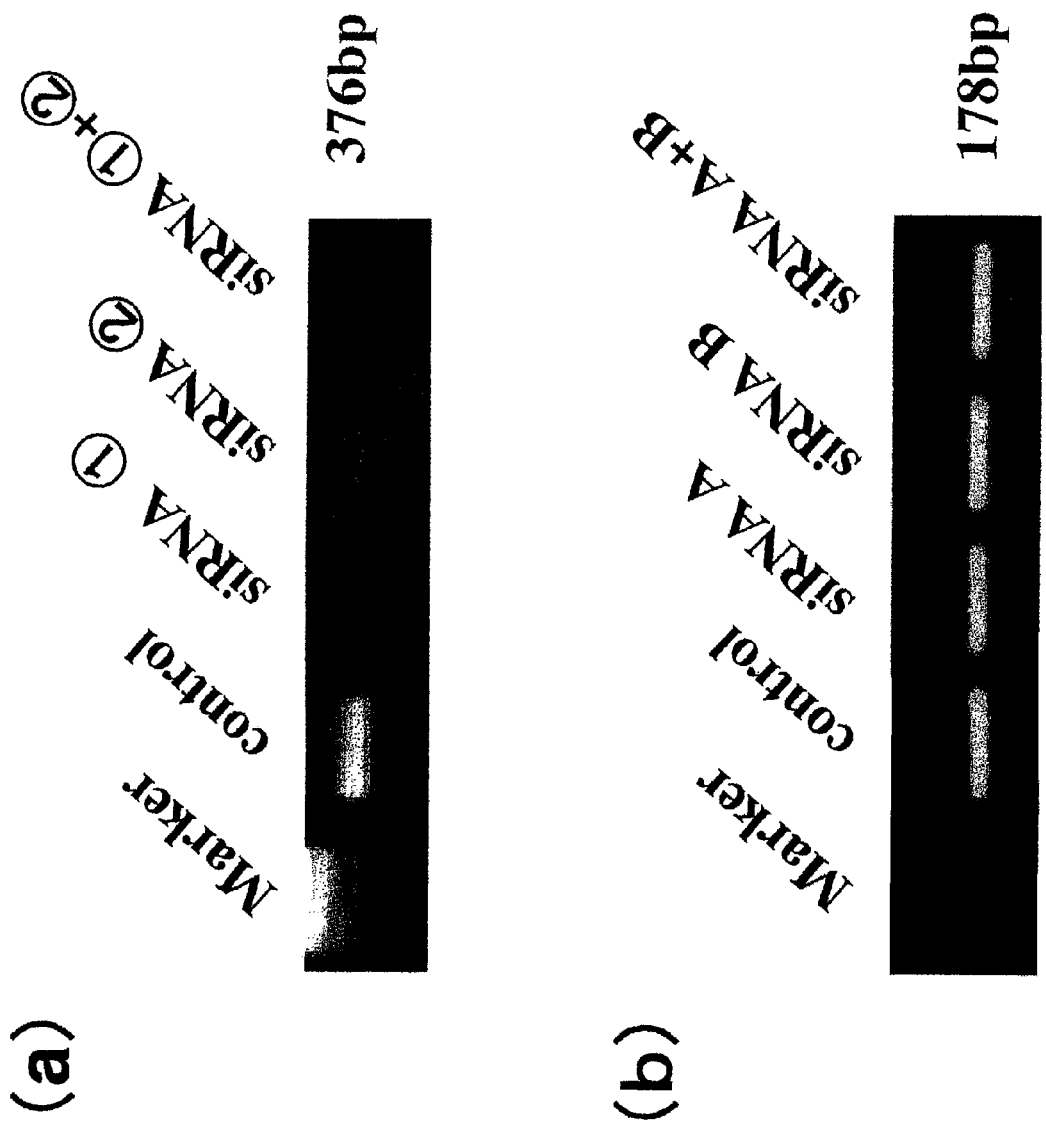
[FIG. 22] Electrophoresis diagram showing expression of RGM376 due to transfection of RGM249 siRNA, and expression of RGM249 due to transfection of RGM376 siRNA.

FIG. 22 is an electrophoresis diagram showing the expression of RGM376 due to the transfection of RGM249 siRNA, and the expression of RGM249 due to the transfection of RGM376 siRNA.

At this time, the method of experimentation is as follows. That is, in the transfection experiments performed in FIG. 21 and FIG. 15, (a) for RGM249 transfection, the expression of RGM376, and (b) for RGM376 transfection, the expression of RGM249, was detected by extracting RNA from the transfected cells and performing RT-PCR.

FIG. 22(*a*) are the results of having observed the influence of transfection with RGM249 siRNA ((1) (indicated within the diagram with a circled number) and (2) (indicated within the diagram with a circled number)), by RT-PCR and electrophoresis. When the expression of the RGM249 gene is suppressed by RGM249 specific siRNA (1), the expression of the RGM376 gene is similarly suppressed. Additionally, among the RGM specific 249 siRNA, when (2) is used alone, and when (1) and (2) are both transfected, the expression suppression effect of the RGM376 gene was lower than when (1) was used alone.

FIG. 22(*b*) are the results of having observed the influence of transfection with RGM376 siRNA (A and B) on the expression of RGM249, by RT-PCR and electrophoresis. When the expression of the RGM376 gene was suppressed by RGM376 specific siRNA, the expression of the RGM249 gene was not suppressed.

From the abovementioned results, it can be seen that the RGM249 gene controls the expression of the RGM376 gene. When doing so, it is presumed that the RGM249 gene controls the expression of the RGM376 gene in the form of promotion. On the other hand, it can be seen that the RGM376 gene does not control the expression of the RGM249 gene.

Figure 24:
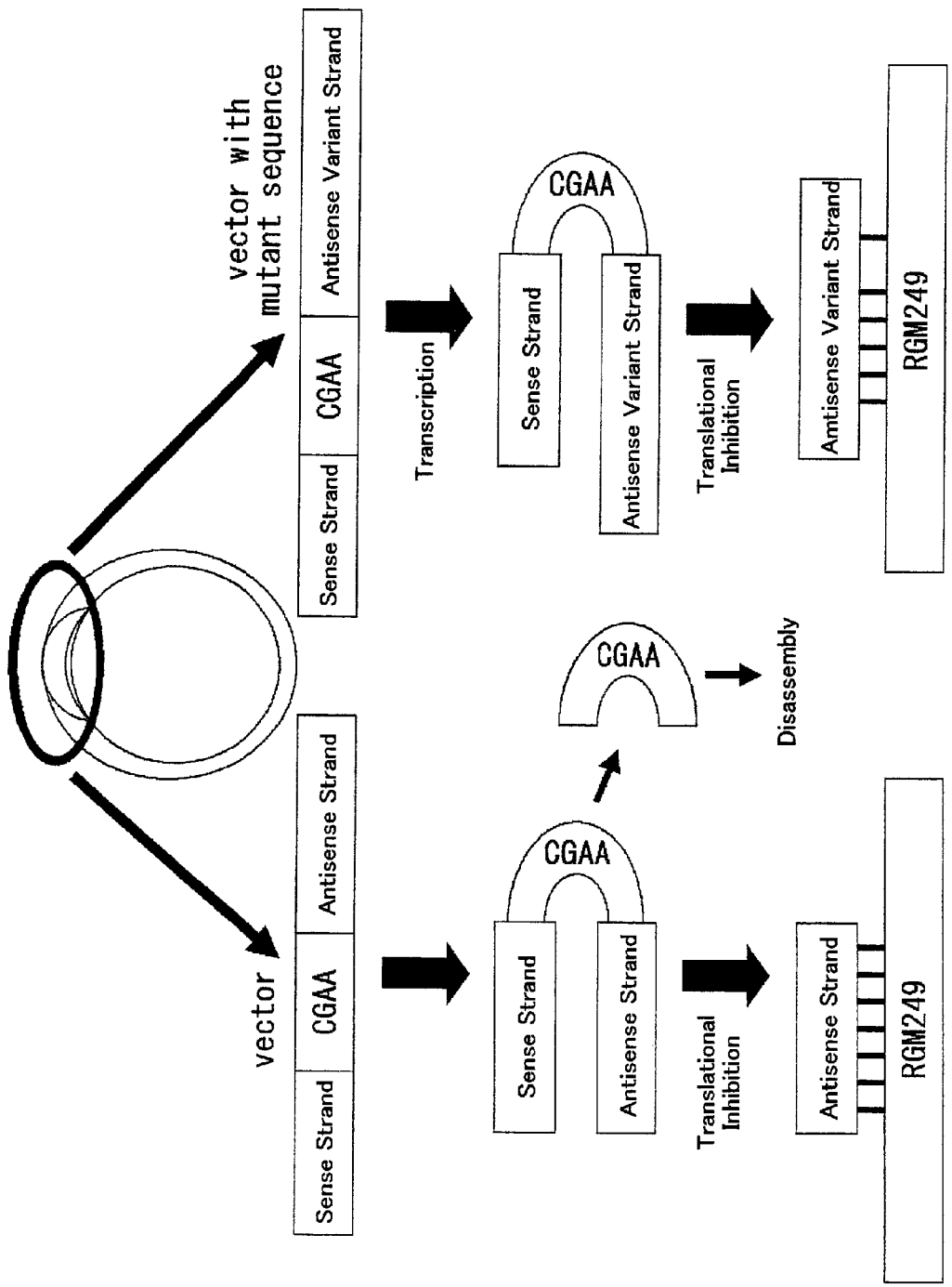
[FIG. 24] Conceptual diagram for explaining mechanism wherein shRNA is generated from plasmids for generating shRNA, and the expression of target gene is inhibited.

FIG. 24 is a conceptual diagram for explaining the mechanism whereby shRNA is generated from plasmids whose purpose is to generate shRNA, and the expression of a target gene is suppressed. As shown in the lefthand side of FIG. 24, a plasmid vector was constructed containing a DNA sequence complementary to the region wherein the RNA sequence comprising CGAA is disposed between the sense strand and the antisense strand of the abovementioned RGM249 siRNA. Further, this DNA sequence was placed downstream of the promoter of the plasmid vector.

FIG. 28 is a figure for explaining the RGM249 shRNA sequence designed based upon gene 2. As shown in the figure, by annealing a single stranded DNA comprising the DNA sequence shown in SEQ ID No. 33, and a single stranded DNA comprising the DNA sequence shown in SEQ ID No. 34, a double stranded DNA wherein these two single stranded DNA are complementarily linked was obtained. Then, a vector for expressing the RGM249 shRNA was produced by implanting this double stranded DNA into a plasmid vector as shown above.

Next, from the DNA sequence of this plasmid vector, an RNA strand wherein an RNA sequence comprising CGAA is disposed between the sense strand and the antisense strand of the abovementioned RGM249 siRNA, a loop is formed in the CGAA portion, and an RGM249 shRNA was generated by forming a stem by linking the sense strand and the antisense strand.

On the other hand, as shown in the righthand side of FIG. 24, an mt plasmid vector was constructed containing a DNA sequence complementary to the region wherein an RNA sequence comprising CGAA is disposed between the sense strand of the abovementioned RGM249 siRNA and an antisense variant strand wherein one of the 8th T residues from the 5' end of the antisense strand is deleted. This DNA sequence was placed downstream of the promoter of the mt plasmid vector.

FIG. 29 is a diagram for explaining the sequence of RGM249 variant shRNA designed based upon gene 2. As shown in this diagram, by annealing a single stranded DNA comprising the DNA sequence shown in SEQ ID No. 35, wherein one of the 8th T residues from the 5' end of the antisense target sequence of the single stranded DNA comprising the DNA sequence shown in SEQ ID No. 33 is deleted, and a single stranded DNA comprising the DNA sequence shown in SEQ ID No. 36, a double stranded DNA linking these two single stranded DNA complementarily was obtained. Then, a vector for expressing RGM249 variant shRNA was produced by implanting this double stranded DNA into a plasmid vector as described above.

Then, from the DNA sequence of this mt plasmid vector, an RGM249 variant shRNA made by disposing an RNA sequence comprising CGAA between the sense strand and an antisense variant strand of the RGM249 siRNA described above, forming a loop at the CGAA portion, and then forming a stem by linking together the sense strand and the antisense strand, was generated. Then, the expression of the RGM249 gene was suppressed by this RGM249 variant shRNA.

Figure 25:
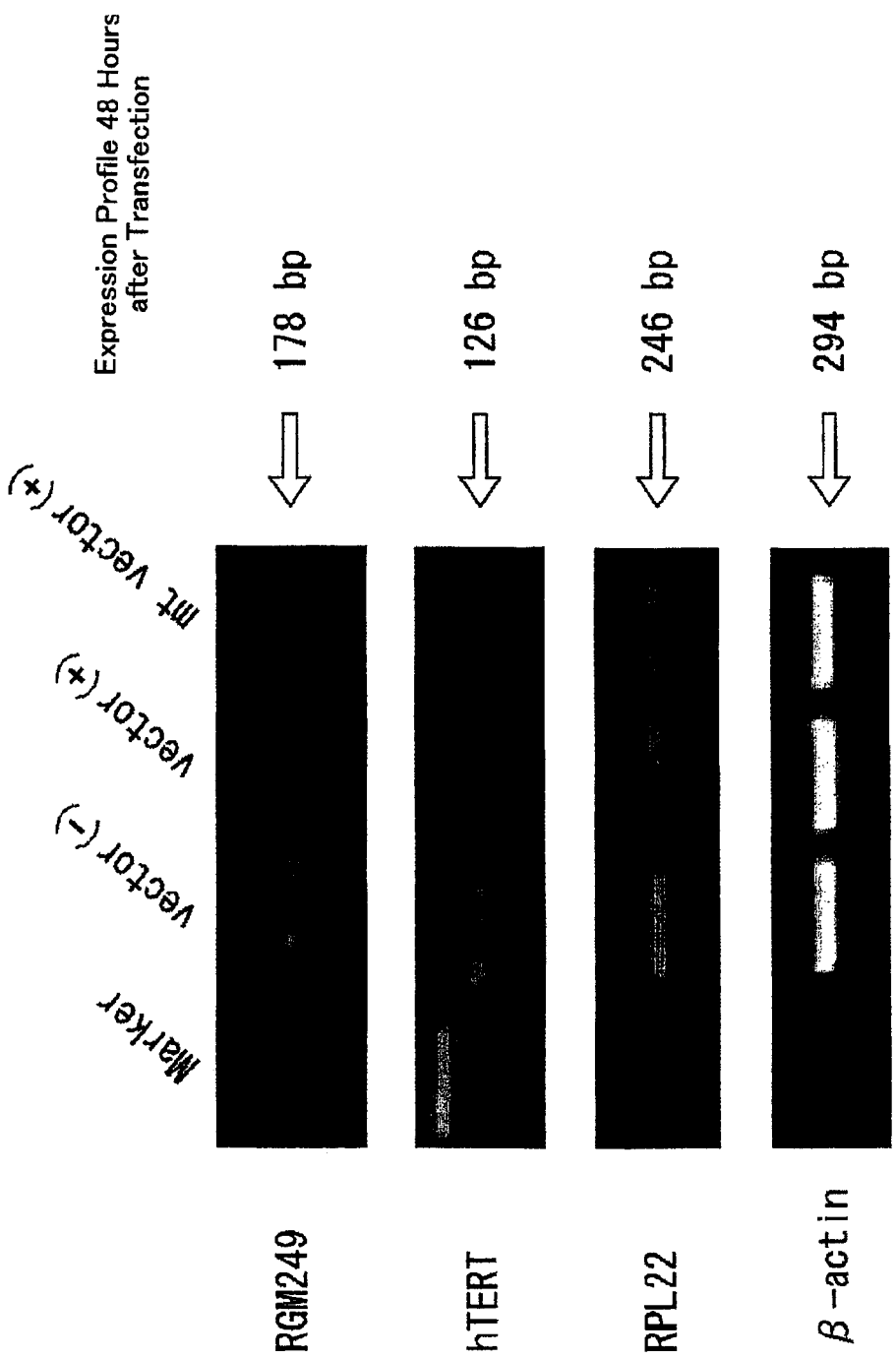
[FIG. 25] Electrophoresis diagram showing expression of mRNA of each gene after transfection with RGM249 shRNA.

FIG. 25 is an electrophoresis diagram showing the expression of mRNA of each gene after transfection with RGM249 shRNA. Plasmid vectors and mt plasmid vectors that generate specific shRNA and variant shRNA designed to suppress the expression of RGM249 as described above were transfected into HLF cells, and RT-PCR and electrophoresis was performed for each of the RGM249, hTERT, RPL22, and the β-actin genes. As a result thereof, in HLF cells wherein the expression of the RGM249 gene was suppressed by shRNA and variant shRNA, the expression of the hTERT gene and the RPL22 gene was also synchronously suppressed.

At this time, the experimental method was as follows. That is, similarly to FIG. 20, plasmid vectors and mt plasmid vectors that generate specific shRNA and variant shRNA designed to suppress the expression of RGM249, described above, designed and synthesized with Block-it RNAi designer, was transfected into the liver cancer cell line HLF, RNA was extracted from transfected cells expressing the shRNA and variant shRNA, RT-PCR was performed, the strength of expression was visualized by electrophoresis, and detected.

Figure 26:
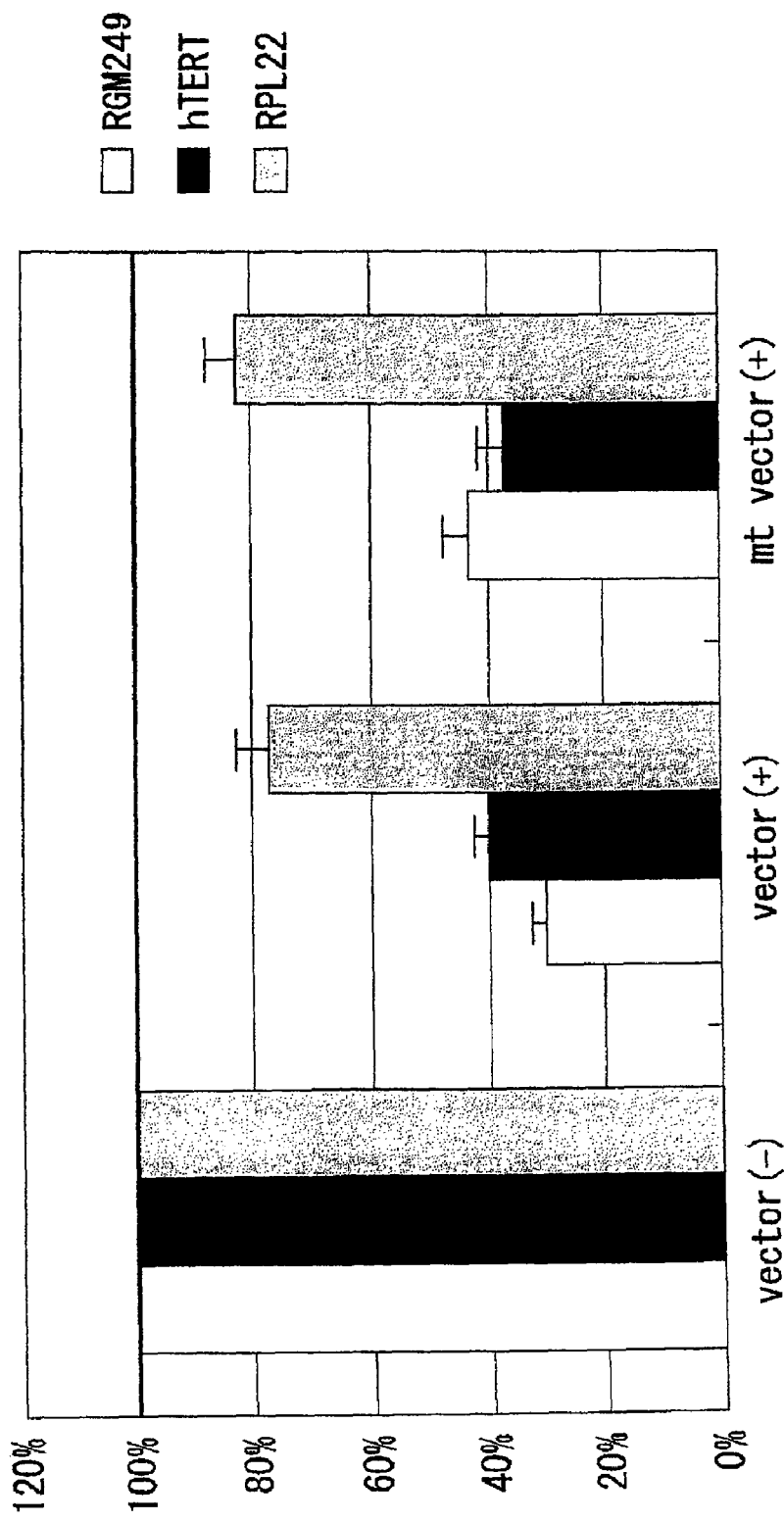
[FIG. 26] Graph summarizing rate of suppression of mRNA expression of each gene after transfection with RGM249 shRNA.

FIG. 26 is a graph summarizing the expression suppression rate of mRNA of each gene after transfection with RGM249 shRNA. As shown in FIG. 26, when the expression of the RGM249 gene is suppressed by plasmid vectors and mt plasmid vectors that generate specific shRNA and variant shRNA designed to suppress the expression of RGM249, described above, the expression of the hTERT gene and the RPL22 gene are also similarly suppressed. Additionally, in cases where one of either the plasmid vectors or the mt plasmid vectors is used, the expression suppression effect against the hTERT gene and the RPL22 gene was approximately the same.

Therefore, if the expression of the RGM249 gene is suppressed by specific shRNA and variant shRNA designed so as to suppress the expression of RGM249, the hTERT gene and the RPL22 gene are also similarly suppressed. Whereby, telomerase activity can be suppressed by specific shRNA and variant shRNA designed so as to suppress the expression of RGM249, and as a result thereof, the canceration of cells can be suppressed.

At this time, the experimental method was as follows. That is, the transfection experiment considered in FIG. 25 was performed three times, the electrophoresis image was image scanned using a densitometer, the measured values were standardized relative to no siRNA, and the degree of suppression of the siRNA gene was shown in a bar graph.

From these experimental results regarding the RGM249 gene, it was found from experiments of the genetic transfection of specific shRNA and variant shRNA designed so as to suppress the expression of RGM249, that shRNA and variant shRNA derived from RGM249 suppress the expression of the hTERT gene and the RPL22 gene. Whereby, there is the possibility that the RGM249 gene is involved in the expression of the hTERT gene and the RPL22 gene.

The present invention has now been explained based upon embodiments. These embodiments are merely examples, and it may be understood by those skilled in the art that various variant examples are possible, and such variant examples are also within the scope of the present invention.

For example, in the abovementioned embodiment, as an siRNA, Stealth (registered trademark) RNAi from Invitrogen Corporation was used, but siRNA or shRNA from other manufacturers, having differing structures, may be used. This is because in such cases also, as long as the expression of the target mRNA can be suppressed, a similar effect can be obtained.

Figure 23:
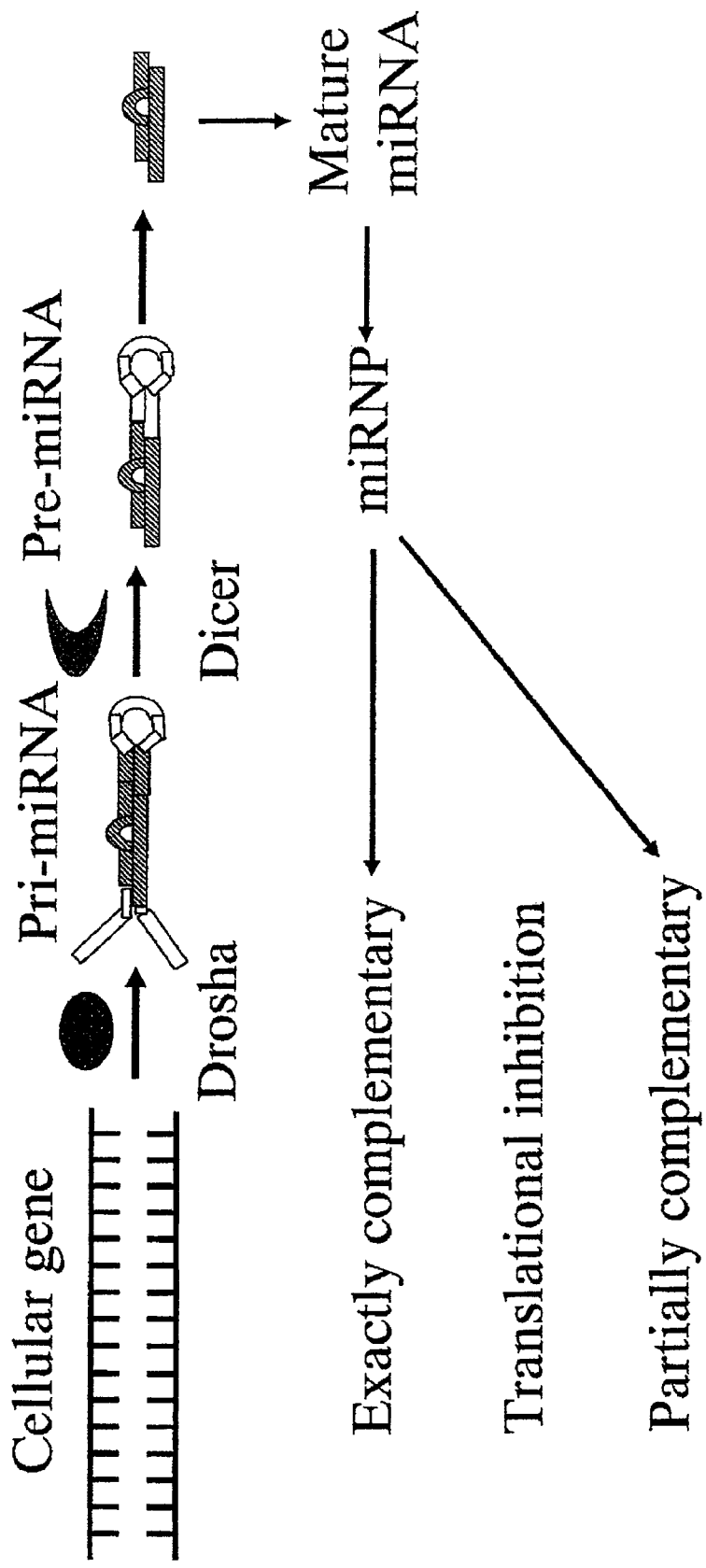
[FIG. 23] Conceptual diagram for explaining the proposed mechanism for translational silencing due to micro RNAs.

For example, in the abovementioned embodiments, siRNA, or siRNA (miRNA) obtained by cleaving siRNA with Dicer was explained, but this is not particularly restricted. For example, in vivo, a mechanism is also presumed where, from a precursor miRNA gene, pri-miRNA of less than approximately 70 bp is generated by Drosha, and becomes pre-miRNA by way of Dicer (see conceptual diagram for explaining the presumed mechanism for translation silencing due to the Micro RNAs of FIG. 23). A similar effect to that of the abovementioned embodiment can be achieved also by a mechanism whereby miRNA obtained through this pri-miRNA and pre-miRNA becomes miRNA and suppresses the translation of the target mRNA within cells.

In the abovementioned embodiments, there were explanations involving RNA, but the RNA can also function as RNP. An RNP (ribonucleoprotein) is a complex that functions by RNA linking to a protein. A mechanism whereby a target is cleaved by forming RNP by these tiny RNA being implanted into RISC can be presumed.

INDUSTRIAL APPLICABILITY

As shown above, since the hTERT expression regulatory gene according to the present invention has the effect of regulating the expression of the telomerase reverse transcriptase gene in mammalian cells, this gene, or specific RNA that suppresses the expression of this gene is useful as a research tool, as a raw material for medicines (cancer treatment agent), and the like.

What is claimed is:

1. An hTERT expression regulatory gene comprising the base sequence shown in SEQ ID No. 2.

2. An isolated hTERT expression regulatory gene consisting of a base sequence wherein one base is deleted from, replaced in, or added to the base sequence shown in SEQ ID No. 2.

3. An hTERT regulatory gene expression vector constructed so as to allow expression, by linking an isolated hTERT expression regulatory gene recited in claim 2 to a vector.

4. An isolated hTERT expression regulatory RNA, being a transcription product of an isolated hTERT regulatory gene recited in claim 2.

5. An isolated hTERT expression regulatory RNA comprising the base sequence shown in SEQ ID No. 4.

6. An isolated hTERT expression regulatory RNA consisting of a base sequence wherein one base is deleted from, replaced in, or added to the base sequence shown in SEQ ID No. 4.

7. An hTERT regulatory gene expression vector constructed so as to allow expression, by linking an hTERT expression regulatory gene recited in claim 1 to a vector.

8. An isolated hTERT expression regulatory RNA, being a transcription product of an isolated hTERT regulatory gene recited in claim 1.

* * * * *

```
                            SEQUENCE LISTING

<160> NUMBER OF SEQ ID NOS: 36

<210> SEQ ID NO 1
<211> LENGTH: 376
<212> TYPE: DNA
<213> ORGANISM: Homo sapiens

<400> SEQUENCE: 1
acattgcctc cggaaataga ccctcccata tgtcaagaat tgggatgctg acatatgtga      60
ggagggcatg aacaactgtt tccctggggt caaattgaaa cctgggcatg tggtgacaac     120
acaattactt caagtcatct ccactgtgac agaggaatga gcacaagaga agggcgagat     180
gtctagagat caagtgacca gtattaatca caatgctgac aacagcgatt gtaaagattg     240
cagaattggc tggcagcttc agaaggcctg agagcatgta cacaagagaa gagttaatgg     300
aagaccatga atgtcccatg cagaccacac gtgggcgagc agcagtctcc atggcatatt     360
tgatcttgca aagcag                                                     376

<210> SEQ ID NO 2
<211> LENGTH: 249
<212> TYPE: DNA
<213> ORGANISM: Homo sapiens

<400> SEQUENCE: 2
ggaaaactaa aatgagagaa tgggtgtcca agaggacaag ttcatgctca cccggtgatg      60
agagtttgat tgcagaataa ggctagacaa agggaagctg aacatgacca aagccatgtg     120
acatcgtatg atcctcgaat ctcacagtat ctatgtatct ataatcagat acatccctag     180
actttccagg aattctggta cttcacgagg atgtgagaag actctgaaca aaataataca     240
ctgctcgtg                                                             249

<210> SEQ ID NO 3
<211> LENGTH: 376
<212> TYPE: RNA
<213> ORGANISM: Homo sapiens

<400> SEQUENCE: 3
acauugccuc cggaaauaga cccucccaua ugucaagaau ugggaugcug acauauguga      60
ggagggcaug aacaacuguu ucccuggggu caaauugaaa ccugggcaug ugguugacaac    120 acaauuacuu caagucaucu ccacugugac agaggaauga gcacaagaga agggcgagau    180
gucuagagau caagugacca guauuaauca caaugcugac aacagcgauu guaaagauug    240
cagaauuggc uggcagcuuc agaaggccug agagcaugua cacaagagaa gaguuaaugg    300
aagaccauga augucccaug cagaccacac gugggcgagc agcagucucc auggcauauu    360
ugaucuugca aagcag                                                    376

<210> SEQ ID NO 4
<211> LENGTH: 249
<212> TYPE: RNA
<213> ORGANISM: Homo sapiens

<400> SEQUENCE: 4
```

-continued

```
ggaaaacuaa aaugagagaa uggguguccs agaggacaag uucaugcuca cccggugaug    60
agaguuugau ugcagaauaa ggcuagacaa agggaagcug aacaugacca aagccaugug   120
acaucguaug auccucgaau cucacaguau cuauguaucu auaaucagau acaucccuag   180
acuuuccagg aauucuggua cuucacgagg augugagaag acucugaaca aaauaauaca   240
cugcucgug                                                          249
```

```
<210> SEQ ID NO 5
<211> LENGTH: 25
<212> TYPE: DNA
<213> ORGANISM: Homo sapiens

<400> SEQUENCE: 5
gcacaagaga agggcgagat gtcta                                         25

<210> SEQ ID NO 6
<211> LENGTH: 25
<212> TYPE: RNA
<213> ORGANISM: Homo sapiens

<400> SEQUENCE: 6
gcacaagaga agggcgagau gucua                                         25

<210> SEQ ID NO 7
<211> LENGTH: 25
<212> TYPE: RNA
<213> ORGANISM: Homo sapiens

<400> SEQUENCE: 7
uagacaucuc gcccuucucu ugugc                                         25

<210> SEQ ID NO 8
<211> LENGTH: 25
<212> TYPE: DNA
<213> ORGANISM: Homo sapiens

<400> SEQUENCE: 8
tccatggcat atttgatctt gcaaa                                         25

<210> SEQ ID NO 9
<211> LENGTH: 25
<212> TYPE: RNA
<213> ORGANISM: Homo sapiens

<400> SEQUENCE: 9
uccauggcau auugaucuu gcaaa                                          25

<210> SEQ ID NO 10
<211> LENGTH: 25
<212> TYPE: RNA
<213> ORGANISM: Homo sapiens

<400> SEQUENCE: 10
uuugcaagau caaauaugcc augga                                         25

<210> SEQ ID NO 11
<211> LENGTH: 25
<212> TYPE: RNA
<213> ORGANISM: Homo sapiens

<400> SEQUENCE: 11
ccuccggaaa uagacccucc cauau                                         25
```

```
<210> SEQ ID NO 12
<211> LENGTH: 25
<212> TYPE: RNA
<213> ORGANISM: Homo sapiens

<400> SEQUENCE: 12
gcugacauau gugaggaggg cauga                                              25

<210> SEQ ID NO 13
<211> LENGTH: 25
<212> TYPE: RNA
<213> ORGANISM: Homo sapiens

<400> SEQUENCE: 13
ugacagagga augagcacaa gagaa                                              25

<210> SEQ ID NO 14
<211> LENGTH: 25
<212> TYPE: RNA
<213> ORGANISM: Homo sapiens

<400> SEQUENCE: 14
agagaagggc gagaugucua gagau                                              25

<210> SEQ ID NO 15
<211> LENGTH: 25
<212> TYPE: RNA
<213> ORGANISM: Homo sapiens

<400> SEQUENCE: 15
gaagggcgag augucuagag aucaa                                              25

<210> SEQ ID NO 16
<211> LENGTH: 25
<212> TYPE: RNA
<213> ORGANISM: Homo sapiens

<400> SEQUENCE: 16
ggcgagaugu cuagagauca aguga                                              25

<210> SEQ ID NO 17
<211> LENGTH: 25
<212> TYPE: RNA
<213> ORGANISM: Homo sapiens

<400> SEQUENCE: 17
gagaugucua gagaucaagu gacca                                              25

<210> SEQ ID NO 18
<211> LENGTH: 25
<212> TYPE: RNA
<213> ORGANISM: Homo sapiens

<400> SEQUENCE: 18
ugucuagaga ucaagugacc aguau                                              25

<210> SEQ ID NO 19
<211> LENGTH: 25
<212> TYPE: RNA
<213> ORGANISM: Homo sapiens

<400> SEQUENCE: 19
gucuagagau caagugacca guauu                                              25
```

```
<210> SEQ ID NO 20
<211> LENGTH: 25
<212> TYPE: RNA
<213> ORGANISM: Homo sapiens

<400> SEQUENCE: 20
gcagaauaag gcuagacaaa gggaa                                                25

<210> SEQ ID NO 21
<211> LENGTH: 25
<212> TYPE: RNA
<213> ORGANISM: Homo sapiens

<400> SEQUENCE: 21
uucccuuugu cuagccuuau ucugc                                                25

<210> SEQ ID NO 22
<211> LENGTH: 25
<212> TYPE: RNA
<213> ORGANISM: Homo sapiens

<400> SEQUENCE: 22
guaugauccu cgaaucucac aguau                                                25

<210> SEQ ID NO 23
<211> LENGTH: 25
<212> TYPE: RNA
<213> ORGANISM: Homo sapiens

<400> SEQUENCE: 23
auacugugag auucgaggau cauac                                                25

<210> SEQ ID NO 24
<211> LENGTH: 25
<212> TYPE: RNA
<213> ORGANISM: Homo sapiens

<400> SEQUENCE: 24
gagaguuuga uugcagaaua aggcu                                                25

<210> SEQ ID NO 25
<211> LENGTH: 25
<212> TYPE: RNA
<213> ORGANISM: Homo sapiens

<400> SEQUENCE: 25
uugauugcag aauaaggcua gacaa                                                25

<210> SEQ ID NO 26
<211> LENGTH: 25
<212> TYPE: RNA
<213> ORGANISM: Homo sapiens

<400> SEQUENCE: 26
ugauugcaga auaaggcuag acaaa                                                25

<210> SEQ ID NO 27
<211> LENGTH: 25
<212> TYPE: RNA
<213> ORGANISM: Homo sapiens

<400> SEQUENCE: 27
uaaggcuaga caaagggaag cugaa                                                25
```

<210> SEQ ID NO 28
<211> LENGTH: 25
<212> TYPE: RNA
<213> ORGANISM: Homo sapiens

<400> SEQUENCE: 28
augugacauc guaugauccu cgaau                                          25

<210> SEQ ID NO 29
<211> LENGTH: 25
<212> TYPE: RNA
<213> ORGANISM: Homo sapiens

<400> SEQUENCE: 29
gugacaucgu augauccucg aaucu                                          25

<210> SEQ ID NO 30
<211> LENGTH: 25
<212> TYPE: RNA
<213> ORGANISM: Homo sapiens

<400> SEQUENCE: 30
gacaucguau gauccucgaa ucuca                                          25

<210> SEQ ID NO 31
<211> LENGTH: 25
<212> TYPE: RNA
<213> ORGANISM: Homo sapiens

<400> SEQUENCE: 31
ucguaugauc cucgaaucuc acagu                                          25

<210> SEQ ID NO 32
<211> LENGTH: 25
<212> TYPE: RNA
<213> ORGANISM: Homo sapiens

<400> SEQUENCE: 32
cguaugaucc ucgaaucuca cagua                                          25

<210> SEQ ID NO 33
<211> LENGTH: 50
<212> TYPE: DNA
<213> ORGANISM: Artificial
<220> FEATURE:
<223> OTHER INFORMATION: sequence for composing RGM249shRNA plasmid
      vector

<400> SEQUENCE: 33
caccgcagaa taaggctaga caaagcgaac tttgtctagc cttattctgc                50

<210> SEQ ID NO 34
<211> LENGTH: 50
<212> TYPE: DNA
<213> ORGANISM: Artificial
<220> FEATURE:
<223> OTHER INFORMATION: sequence for composing RGM249shRNA plasmid
      vector

<400> SEQUENCE: 34
aaaagcagaa taaggctaga caaagttcgc tttgtctagc cttattctgc                50

<210> SEQ ID NO 35
<211> LENGTH: 20

```
<212> TYPE: DNA
<213> ORGANISM: Artificial
<220> FEATURE:
<223> OTHER INFORMATION: sequence for composing RGM249 mutant shRNA
      plasmid vector

<400> SEQUENCE: 35
ctttgtcagc cttattctgc                                               20

<210> SEQ ID NO 36
<211> LENGTH: 19
<212> TYPE: DNA
<213> ORGANISM: Artificial
<220> FEATURE:
<223> OTHER INFORMATION: sequence for composing RGM249 mutant shRNA
      plasmid vector

<400> SEQUENCE: 36
gcagaataag gctgacaaa                                                19
```